US012806225B2

(12) United States Patent
He et al.

(10) Patent No.: US 12,806,225 B2
(45) Date of Patent: Nov. 24, 2026

(54) CHEMICALLY MODIFIED TRANSFER RNA-DERIVED SMALL RNAS (TSRNAS) TO TARGET PATHOGENIC BACTERIA

(71) Applicants: ADA Forsyth Institute, Inc., Cambridge, MA (US); Northeastern University, Boston, MA (US)

(72) Inventors: Xuesong He, Cypress, CA (US); Jiahe Li, Medford, MA (US); Wenyuan Shi, Winchester, MA (US)

(73) Assignees: ADA Forsyth Institute, Inc., Cambridge, MA (US); Northeastern University, Boston, MA (US)

( * ) Notice: Subject to any disclaimer, the term of this patent is extended or adjusted under 35 U.S.C. 154(b) by 1002 days.

(21) Appl. No.: 17/907,833

(22) PCT Filed: Feb. 26, 2021

(86) PCT No.: PCT/US2021/019890
§ 371 (c)(1),
(2) Date: Aug. 29, 2022

(87) PCT Pub. No.: WO2021/173986
PCT Pub. Date: Sep. 2, 2021

(65) Prior Publication Data

US 2023/0165889 A1 Jun. 1, 2023

Related U.S. Application Data

(60) Provisional application No. 62/983,125, filed on Feb. 28, 2020.

(51) Int. Cl.
*C07H 21/02* (2006.01)
*A61K 31/7125* (2006.01)
*A61P 31/04* (2006.01)

(52) U.S. Cl.
CPC .......... *A61K 31/7125* (2013.01); *A61P 31/04* (2018.01)

(58) Field of Classification Search
CPC .......................... C12N 15/113; C12N 2310/14
See application file for complete search history.

(56) References Cited

U.S. PATENT DOCUMENTS 8,173,616 B2 * 5/2012 Anderson ............... A61P 31/20
536/24.1

FOREIGN PATENT DOCUMENTS

WO WO-2012/006551 A2 1/2012
WO WO-2014144844 A1 9/2014
WO WO-2016065349 A2 * 4/2016 ........... C12N 15/113
WO WO-2016/069641 A1 5/2016
WO WO-2019173942 A1 9/2019
WO WO-2021/173986 A1 9/2021

OTHER PUBLICATIONS

Kraynack et al. (RNA, 2006, 12, 163-176).*
Oberbauer et al. (Genes, 2018, 9, 607, 1-36).*
He et al. (Journal of Dental Research, 2018, 97, 11, 1236-1243).*
He et al., "Human tRNA-Derived Small RNAs Modulate Host-Oral Microbial Interactions," J Dent Res, 97(11): 1236-1243 (2018).
International Preliminary Report on Patentability for International Application No. PCT/US2021/019890 mailed May 20, 2021.
Iwamoto et al., "Control of phosphorothioate stereochemistry substantially increases the efficacy of antisense oligonucleotides," Nat Biotechnol, 35, (11 pages) (2017).
Oberbauer et al., "tRNA-Derived Small RNAs: Biogenesis, Modification, Function, and Potential Impact on Human Disease Development," Genes, 9(12): 1-36 (2018).
Hendel et al., "Chemically modified guide RNAs enhance CRISPR-Cas genome editing in human primary cells." Nature Biotechnology 33(9) (2015): 985-989.
Kapatral et al., "Genome sequence and analysis of the oral bacterium Fusobacterium nucleatum strain ATCC 25586." Journal of Bacteriology 184(7) (2002): 2005-2018.
Kurreck et al., "Design of antisense oligonucleotides stabilized by locked nucleic acids." Nucleic Acids Research 30(9) (2002): 1911-1918.
Park et al., "Characterization of Fusobacterium nucleatum ATCC 23726 adhesins involved in strain-specific attachment to Porphyromonas gingivalis." International Journal of Oral Science 8(3) (2016): 138-144.
Supplementary European Search Report for EP Application No. 21760796.9 dated Apr. 3, 2025.
Yang et al., "Targeting Fusobacterium nucleatum through chemical modifications of host- derived transfer RNA fragments." The ISME Journal 17(6) (2023): 880-890.

* cited by examiner

*Primary Examiner* — Amy Rose Hudson
(74) *Attorney, Agent, or Firm* — Foley Hoag LLP; Hathaway P. Russell; Tracy L. Vrablik

(57) ABSTRACT

Provided herein are chemically modified transfer RNA-derived Small RNAs (tsRNAs) that target *Fusobacterium nucleatum* and methods of use thereof.

12 Claims, 18 Drawing Sheets

Specification includes a Sequence Listing.

FIG. 2A

| | |
|---|---|
| tsRNA-000794 (AS41) | CCGGCUAGCUCAGUCGGUAGAGCAUGAG[mA] (SEQ ID NO: 1) |
| tsRNA-020498 (AS42) | GGGGGUAUAGCUCAGUGGUAGAGCA[mU] (SEQ ID NO: 2) |

FIG.3

| | | |
|---|---|---|
| AS38 | tsRNA-000794 (three 2'-OMe and 2PS) | [mC]*[mC]*[mG]GCUAGCUCAGUCGGUAGAGCAUG[mA]*[mG]*[mA] (SEO ID NO: 3) |
| AS39 | tsRNA-020498 (three 2'-OMe and 2PS) | [mG]*[mG]*[mG]GGUAUAGCUCAGUGGGUAGAG[mC]*[mA]*[mU] (SEO ID NO: 4) |
| AS40 | scramble RNA (three 2'-OMe and 2PS) | [mG]*[mG]*[mA]CGACAAGUUCGUGACGAGCGCAU[mC]*[mU]*[mG] (SEO ID NO: 5) |
| AS41 | tsRNA-000794 (one 2'-OMe at 3') | CCGGCUAGCUCAGUCGGUAGAGCAUGAG[mA] (SEO ID NO: 1) |
| AS42 | tsRNA-020498 (one 2'-OMe at 3') | GGGGGUAUAGCUCAGUGGGUAGAGCA[mU] (SEO ID NO: 2) |
| AS43 | scramble RNA (one 2'-OMe at 3') | GGACGACAAGUUCGUGACGAGCGCAUCU[mG] (SEO ID NO: 6 |
| AS47 | tsRNA-000794 (full 2'-OMe and 2PS) | [mC]*[mC]*[mG][mG][mC][mU][mA][mG][mC][mU][mC][mA][mG][mU][mC][mG][mG][mU][mA][mG][mA][mG][mC][mA][mU][mG][mA]*[mG]*[mA] (SEO ID NO: 7) |
| AS48 | tsRNA-020498 (full 2'-OMe and 2PS) | [mG]*[mG]*[mG][mG][mG][mU][mA][mU][mA][mG][mC][mU][mC][mA][mG][mU][mG][mG][mG][mU][mA][mG][mA][mG][mC]*[mA]*[mU] (SEO ID NO: 8) |
| AS49 | scramble RNA (full 2'-OMe and 2PS) | [mG]*[mG]*[mA][mC][mG][mA][mC][mA][mA][mG][mU][mU][mC][mG][mU][mG][mA][mC][mG][mA][mG][mC][mG][mC][mA][mU][mC]*[mU]*[mG] (SEO ID NO: 9) |

Three 2′-OMe and two PS bonds (AS38, 39 and 40)

One 2′-OMe at 3' (naturally occurring, AS41, 42 and 43)

Full 2′-OMe and two PS bonds (AS47, 48 and 49)

Three 2′-OMe and two PS bonds (AS38, 39 and 40)

One 2′-OMe at 3' (naturally occurring, AS41, 42 and 43)

Full 2′-OMe and two PS bonds (AS47, 48 and 49)

Combination of *Fn*-targeting tsRNAs modified with three 2′-OMe and two PS bonds (AS38+AS39)

Combination of *Fn*-targeting tsRNAs modified with one 2′-OMe at 3' (naturally occurring) (AS41+AS42)

*Fusobacterium nucleatum* (Fn23726)

*Streptococcus mitis*

AS59: Cy3-tsRNA-000794-MOD
AS60: Cy3-tsRNA-020498-MOD
AS61: Cy3-tsRNA-scrambled-MOD

SEQUENCE LISTING

```
<160> NUMBER OF SEQ ID NOS: 9

<210> SEQ ID NO 1
<211> LENGTH: 29
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1

ccggcuagcu cagucgguag agcaugaga                                      29


<210> SEQ ID NO 2
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2

gggggauaag cucagugggu agagcau                                        27


<210> SEQ ID NO 3
<211> LENGTH: 29
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3

ccggcuagcu cagucgguag agcaugaga                                      29


<210> SEQ ID NO 4
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4

gggggauaag cucagugggu agagcau                                        27


<210> SEQ ID NO 5
<211> LENGTH: 29
<212> TYPE: RNA
<213> ORGANISM: Artificial Sequence
```

-continued

```
<220> FEATURE:
<223> OTHER INFORMATION: Description of Artificial Sequence: Synthetic
      oligonucleotide

<400> SEQUENCE: 5

ggacgacaag uucgugacga gcgcaucug                                        29


<210> SEQ ID NO 6
<211> LENGTH: 29
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6

ggacgacaag uucgugacga gcgcaucug                                        29


<210> SEQ ID NO 7
<211> LENGTH: 29
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7

ccggcuagcu cagucgguag agcaugaga                                        29


<210> SEQ ID NO 8
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8

gggggguauag cucagugggu agagcau                                         27


<210> SEQ ID NO 9
<211> LENGTH: 29
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9

ggacgacaag uucgugacga gcgcaucug                                        29
```

CHEMICALLY MODIFIED TRANSFER RNA-DERIVED SMALL RNAS (TSRNAS) TO TARGET PATHOGENIC BACTERIA

CROSS-REFERENCE TO RELATED APPLICATIONS

This application is a 371 National Stage Application based off International Patent Application No. PCT/US21/19890, filed Feb. 26, 2021, which claims the benefit of U.S. Provisional Application No. 62/983,125, filed Feb. 28, 2020, the entire contents of which are incorporated by reference herein in their entirety.

STATEMENT REGARDING FEDERALLY SPONSORED RESEARCH OR DEVELOPMENT

This invention was made with government support under grant number R01DE026186and R03DE031329 awarded by The National Institutes of Health. The U.S. government has certain rights in the invention.

SEQUENCE LISTING

The instant application contains a Sequence Listing which has been submitted electronically in ASCII format and is hereby incorporated by reference in its entirety. Said ASCII copy, created on Oct. 18, 2022, is named FIR-03301_SL.txt and is 2,521 bytes in size.

BACKGROUND

The human body and its resident microbiota form a complex and balanced community. The use of antibiotics remains the sole solution to treat infectious diseases caused by pathogenic and opportunistic microbes. The benefits that antibiotics have brought to modern medicine are unquestionable; however, their overuse comes with consequences, including the potential for secondary infections by opportunistic pathogens and the spread of antibiotic resistance. Emerging evidence suggests that in addition to small molecules such as antibiotics, small regulatory noncoding RNAs (sRNAs) might play an important role in host-mediated defense against bacterial pathogens. Notably, recent studies indicate that sRNAs could be used by animals and plants as defense mechanisms targeting pathogens by silencing or modulating virulence-related genes.

Thus, sRNAs that are capable of selectively targeting pathogenic bacteria would have great potential for use as antibiotics.

SUMMARY

In certain aspects, provided herein are chemically-modified RNAs that selectively target pathogenic bacteria (e.g., *Fusobacterium nucleatum*) and/or selectively induces RNA-mediated growth inhibition and/or cell death. In some aspects, provided herein are pharmaceutical compositions comprising such chemically-modified RNAs, methods of using such chemically-modified RNAs to treat pathogenic bacteria-associated disease (e.g., periodontal diseases, preterm birth issues and colorectal cancer) and/or to kill pathogenic bacteria.

In certain aspects, provided herein are chemically modified tsRNAs comprising a nucleic acid sequence that is at least 60% identical (e.g., at least 65% identical, at least 70% identical, at least 75% identical, at least 80% identical, at least 85% identical, at least 90% identical, at least 92% identical, at least 94% identical, at least 96% identical, at least 98% identical) to SEQ ID NO 1 or 2. In certain embodiments, the chemically modified tsRNAs comprise at least 15 (e.g., at least 15, at least 16, at least 17, at least 18, at least 19, at least 20, at least 21, at least 22, at least 23, at least 24, at least 25, at least 26, at least 27) consecutive nucleotides of SEQ ID NO 1 or 2. In some embodiments, the chemically modified tsRNAs comprise a nucleic acid sequence of SEQ ID NO 1 or 2. In some embodiments, the chemically modified tsRNAs provided herein have a sequence consisting essentially of SEQ ID NO 1 or 2. In certain embodiments, the chemically modified tsRNAs provided herein have a sequence consisting of SEQ ID NO 1 or 2.

In certain embodiments, the chemically modified tsRNAs provided herein are no more than 60 nucleotides in length (e.g., no more than 60 nucleotides in length, no more than 55 nucleotides in length, no more than 50 nucleotides in length, no more than 45 nucleotides in length, no more than 40 nucleotides in length, no more than 35 nucleotides in length, no more than 34 nucleotides in length, no more than 33 nucleotides in length, no more than 32 nucleotides in length, no more than 31 nucleotides in length, no more than 30 nucleotides in length, or no more than 29 nucleotides in length).

In some embodiments, the chemically modified tsRNAs provided herein are able to inhibit growth of *F. nucleatum*. In some embodiments, the chemically modified tsRNAs provided herein are able to induce death of *F. nucleatum*. In some embodiments, the chemically modified tsRNAs inhibit growth and/or induce cell death of *F. nucleatum* in vitro. In certain embodiments, the chemically modified tsRNAs inhibit growth and/or induce cell death of *F. nucleatum* in vivo (e.g., in a human and/or an animal model).

In some embodiments, the chemically modified tsRNAs provided herein comprise one or more chemical modifications. In some embodiments, the chemically modified tsRNAs comprise one or more (e.g., at least 1, 2, 3, 4, 5, 6, 7, 8, 9, 10 11, 12, 13, 14, 15, 16, 17, 18, 19, 20, 21, 22, 23, 24, 25, or 26) 2' sugar substitutions (e.g. a 2'-fluoro, a 2'-amino, or a 2'-O-methyl substitution). In some embodiments, the chemically modified tsRNA comprises at least one (e.g., 1, 2, 3, 4, 5, 6, 7, 8, 9, 10 11, 12, or 13) 2'-O-methylated nucleotide positioned at the 3' end. In certain embodiments, the chemically modified tsRNA comprises one, two, or three consecutive 2'-O-methylated nucleotides positioned at the 3' end. In some embodiments, the chemically modified tsRNA comprises at least one (e.g., 1, 2, 3, 4, 5, 6, 7, 8, 9, 10 11, 12, or 13) 2'-O-methylated nucleotide positioned at the 5' end. In certain embodiments, the chemically modified tsRNA comprises one, two, or three consecutive 2'-O-methylated nucleotides positioned at the 3' end. In certain embodiments, the chemically modified tsRNA comprises one, two, or three consecutive 2'-O-methylated nucleotides positioned at the 5' end. In specific embodiments, the chemically modified tsRNA comprises three consecutive 2'-O-methylated nucleotides positioned at the 5' end and three consecutive 2'-O-methylated nucleotides positioned at the 3' end. In some embodiments, not all nucleotides of the chemically modified tsRNA are 2'-O-methylated.

In some embodiments, the chemically modified tsRNAs comprise one or more (e.g., at least 1, 2, 3, 4, 5, 6, 7, 8, 9, 10 11, 12, 13, 14, 15, 16, 17, 18, 19, 20, 21, 22, 23, 24, 25, or 26) phosphorothioate internucleotide bonds. In some embodiments, the chemically modified tsRNA comprises at least one (e.g., 1, 2, 3, 4, 5, 6, 7, 8, 9, 10 11, 12, or 13)

phosphorothioate internucleotide bond at the 3' end. In some embodiments, the chemically modified tsRNA comprises at least one (e.g., 1, 2, 3, 4, 5, 6, 7, 8, 9, 10 11, 12, or 13) phosphorothioate internucleotide bond at the 5' end. In certain embodiments, the chemically modified tsRNA comprises one or two consecutive phosphorothioate internucleotide bonds at the 3' end. In certain embodiments, the chemically modified tsRNA comprises one or two consecutive phosphorothioate internucleotide bonds at the 5' end. In specific embodiments, the chemically modified tsRNA comprises two consecutive phosphorothioate internucleotide bonds at the 5' end and two consecutive phosphorothioate internucleotide bonds at the 3' end.

In some embodiments, chemically modified tsRNA comprises three consecutive 2'-O-methylated nucleotides positioned at the 5' end, three consecutive 2'-O-methylated nucleotides positioned at the 3' end, two consecutive phosphorothioate internucleotide bonds at the 3' end, and two consecutive phosphorothioate internucleotide bonds at the 5' end. In specific embodiments, the chemically modified tsRNA is AS38 or AS39.

In some embodiments, the chemically modified tsRNA has an increased stability compared to a naturally occurring tsRNA with the same sequence. In some embodiments, the chemically modified tsRNA increases growth inhibition of *Fusobacterium nucleatum* (Fn) compared to a naturally occurring tsRNA with the same sequence. In some embodiments, the chemically modified tsRNA increases growth inhibition of *Fusobacterium nucleatum* (Fn) by at least 1000-fold. In some embodiments, the chemically modified tsRNA induced growth inhibition of *Fusobacterium nucleatum* (Fn) at nanomolar range. In some embodiments, the chemically modified tsRNA does not inhibit growth of *Streptococcus mitis*. In some embodiments, the chemically modified tsRNA does not inhibit growth of *Porphyromonas gingivalis*. In some embodiments, the chemically modified tsRNA is internalized by *Fusobacterium nucleatum*. In some embodiments, the chemically modified tsRNA is internalized by *Fusobacterium nucleatum* strain 23726 or 25586. In some embodiments, the chemically modified tsRNA is not internalized by *Streptococcus mitis*.

In certain aspects, provided herein are pharmaceutical compositions comprising at least one chemically modified tsRNA (e.g., a therapeutically effective amount of a chemically modified tsRNA) provided herein. In some embodiments, the pharmaceutical compositions provided herein comprise two chemically modified tsRNAs: one is selected from AS38 and AS41, and the other one is selected from AS39 and AS42. In some embodiments, the pharmaceutical compositions provided herein comprise two chemically modified tsRNAs: AS38 and AS39. In some embodiments, the pharmaceutical compositions provided herein comprise two chemically modified tsRNAs: AS41 and AS42. In some embodiments, the pharmaceutical compositions provided herein further comprise a pharmaceutically acceptable carrier. In some embodiments, the pharmaceutical compositions provided herein are formulated for parenteral administration.

In certain embodiments, the pharmaceutical compositions provided herein are for use in treating *F. nucleatum* infection. In certain embodiments, the pharmaceutical compositions provided herein are for use in treating *F. nucleatum*-associated disease. In some embodiments, the *F. nucleatum*-associated disease is a periodontal disease. In some embodiments, the *F. nucleatum*-associated disease is a preterm birth issue. In some embodiments, the *F. nucleatum*-associated disease is a colorectal cancer.

In certain aspects, provided herein is a method of treating *F. nucleatum* infection in a subject, the method comprising administering to the subject a chemically modified tsRNA (e.g., a therapeutically effective amount of a chemically modified tsRNA) or a pharmaceutical composition provided herein. In certain aspects, provided herein is a method of treating *F. nucleatum*-associated disease in a subject, the method comprising administering to the subject a chemically modified tsRNA (e.g., a therapeutically effective amount of a chemically modified tsRNA) or a pharmaceutical composition provided herein. In some embodiments, the *F. nucleatum*-associated disease is a periodontal disease. In some embodiments, the *F. nucleatum*-associated disease is a preterm birth issue. In some embodiments, the *F. nucleatum*-associated disease is a colorectal cancer. In some embodiment, the method comprising administering to the subject two chemically modified tsRNAs: one is selected from AS38 and AS41, and the other one is selected from AS39 and AS42 (e.g., the combination of AS38 and AS39, or the combination of AS41 and AS42). In some embodiments, the chemically modified tsRNA or the pharmaceutical composition is administered in a pharmaceutically acceptable formulation. In some embodiments, the administration is parenteral administration (e.g., subcutaneous administration). In some embodiments, the subject is a human.

In some embodiments, the therapeutic methods for treating a subject with *Fusobacterium nucleatum*-associated colorectal cancer further comprise administering to the subject an additional cancer therapy. In some embodiments, the additional cancer therapy comprises chemotherapy. In certain embodiments, the additional cancer therapy comprises radiation therapy. In some embodiments, the additional cancer therapy comprises surgical removal of a tumor. In certain embodiments, the additional cancer therapy comprises administration of an immune checkpoint inhibitor, e.g., an anti-PD-1 antibody, an anti-PD-L1 antibody, an anti-PD-L2 antibody, or an anti-CTLA4 antibody) to the subject.

In certain aspects, provided herein is a method of killing *Fusobacterium nucleatum*, the method comprising contacting *Fusobacterium nucleatum* with at least one chemically modified tsRNA provided herein. In some embodiments, *Fusobacterium nucleatum* is killed when contacted with the chemically modified tsRNA in vitro. In certain embodiments, *Fusobacterium nucleatum* is killed when contacted with the chemically modified tsRNA in vivo (e.g., in a human and/or an animal model). In some embodiment, the method comprising contacting *Fusobacterium nucleatum* with two chemically modified tsRNAs: one is selected from AS38 and AS41, and the other one is selected from AS39 and AS42 (e.g., the combination of AS38 and AS39, or the combination of AS41 and AS42).

BRIEF DESCRIPTION OF FIGURES

FIG. 1B is adapted from Brennan C. A. and Garrett W. S. (2019) *Nat. Rev. Microbiol.* 17(3):156-166.

FIG. 2A shows that two host-derived tsRNAs, tsRNA-000794 and tsRNA-020498, were identified in salivary exosomes from healthy human subjects. Figure discloses SEQ ID NOS 1 and 2, respectively, in order of appearance.

FIGS. 2B-2E are adapted from He et al. (2018) *Journal of Dental Research* 97(11):1236-1243.

FIG. 3 shows a list of chemically modified and naturally occurring tsRNAs used in the invention. AS41 and 42 are mimics of naturally occurring transfer RNA-derived small RNAs (tsRNAs) identified in human saliva and oral keratinocytes, while others in the table are chemical modified. [mA], [mU], [mC] and [mG] denote 2'-O-methylation, where a methyl group is added to the 2' hydroxyl of the ribose moiety of a nucleoside to increase its resistance against nuclease-mediated degradation. * indicates a phosphorothioate (PS) bond, where a sulfur atom substitutes for a non-bridging oxygen in the phosphate backbone of an oligo. This modification renders the internucleotide linkage resistant to nuclease degradation. Figure discloses SEQ ID NOS 3-5, 1-2, and 6-9, respectively, in order of appearance.

FIG. 6A shows that chemical modification (2'-O-methylation at three 5' and 3' terminal nucleotides along with two PS bonds) significantly increased the stability of Fn-targeting tsRNAs. FIG. 6B shows that chemical modified Fn-targeting tsRNAs inhibited *Fusobacterium nucleatum* growth at nanomolar range. FIG. 6C shows that chemical modified Fn-targeting tsRNAs did not inhibit *Streptococcus mitis*, indicating the high specificity. FIG. 6D shows that chemical modified Fn-targeting tsRNAs did not inhibit *Porphyromonas gingivalis*, indicating the high specificity.

FIG. 9A shows that Fn 23726 uptook more Cy3-labeled tsRNA-000794-MOD which is consistent with the best killing effect of the modified tsRNA-000794. Quantitative analysis of the fluorescence intensity was performed by student unpaired t-test. FIG. 9B shows confocal imaging (Airyscan) of the uptake of the Cy3-labeled tsRNA-000794 by Fn 23726 by showing the signal of tsRNAs accumulated in the cytoplasm.

FIG. 9C shows confocal imaging (Airyscan) which shows that in the case of *Streptococcus mitis*, tsRNA was accumulated in the cell membrane area as granules, but not inside of the cytoplasm.

DETAILED DESCRIPTION

General

Figure 1A:
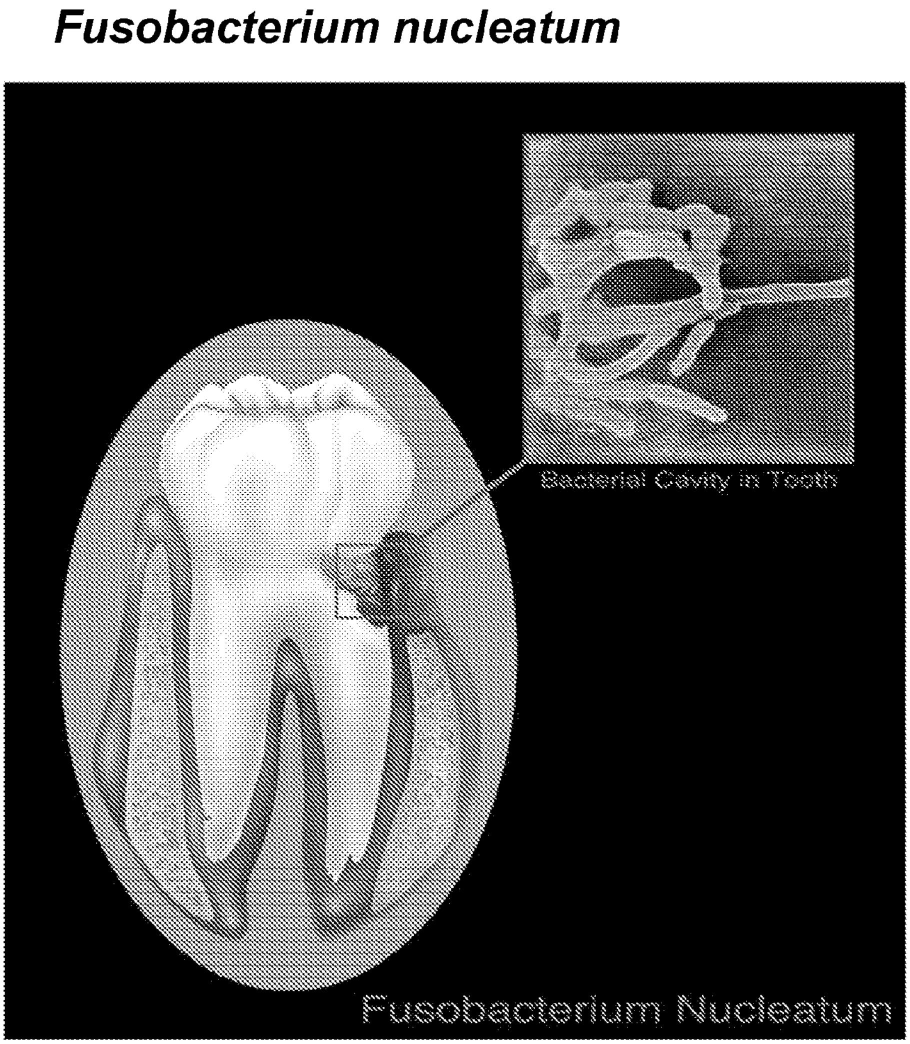
FIG. 1A shows that *Fusobacterium nucleatum* is a gram-negative microorganism that lives in human oral cavity and cause opportunistic infections such as periodontal disease.

The present invention is based, at least in part, on the discovery of naturally-derived small RNA sequences that are able to specifically target *Fusobacterium nucleatum* with minimal side effects on health-associated bacteria. In addition, it was demonstrated herein that unique chemical modifications on the small RNAs that do not exist in nature can enhance the potency by ~1000 fold, which paved way for clinical applications of these small RNAs. This invention therefore developed a new mode of "antibiotics" that exhibited selectivity towards pathogenic bacteria, *Fusobacterium nucleatum* specifically, but spare health-associated microbes in the body. It can be used for *Fusobacterium nucleatum*-associated diseases, such as periodontal diseases (e.g., periodontitis), preterm birth issues and colorectal cancer. It can address problems associated with usage of antibiotics to treat bacterial infection including but not limited to antibiotic resistance and lack of selectivity. There are several advantages of the present invention. First, these small RNAs induce sequence-dependent RNA-mediated bacterial growth inhibition and therefore have much higher selectivity over antibiotics which typically target a generic cellular structures such as cell wall or protein synthesis machinery. Due to their selectively, using small RNAs has minimal deleterious effect on the health-associated bacteria and the ecosystem in human-microbiota interactions. Second, multiple different RNA mimics can be designed to simultaneously target the same pathogenic bacteria to avoid potential emergence of drug-resistant bacteria. Third, RNA mimics can be programmed via different chemical modifications to have different half-lives such that once they are excreted from the body, they are unlikely to contaminate our environment.

In certain aspects, provided herein are chemically-modified RNAs that selectively target pathogenic bacteria (e.g., *Fusobacterium nucleatum*) and/or selectively induces RNA-mediated growth inhibition and/or cell death. In some aspects, provided herein are pharmaceutical compositions comprising such chemically-modified RNAs, methods of using such chemically-modified RNAs to treat pathogenic bacteria-associated disease (e.g., periodontal diseases, preterm birth issues and colorectal cancer) and/or to kill pathogenic bacteria.

Definitions

For convenience, certain terms employed in the specification, examples, and appended claims are collected here.

The articles "a" and "an" are used herein to refer to one or to more than one (e.g., to at least one) of the grammatical object of the article. By way of example, "an element" means one element or more than one element.

As used herein, the term "chemically modified tsRNA" refers to a short (e.g., less than 50 bases), single stranded RNA that derived from transfer RNA (tRNA) and comprise at least one chemical modification.

The term "binding" or "interacting" refers to an association, which may be a stable association, between two molecules, e.g., between an chemically modified tsRNA and target, e.g., due to, for example, electrostatic, hydrophobic, ionic and/or hydrogen-bond interactions under physiological conditions.

As used herein, two nucleic acid sequences "complement" one another or are "complementary" to one another if they base pair one another at each position.

As used herein, two nucleic acid sequences "correspond" to one another if they are both complementary to the same nucleic acid sequence.

The term "modulation" or "modulate", when used in reference to a functional property or biological activity or process (e.g., enzyme activity or receptor binding), refers to the capacity to either up regulate (e.g., activate or stimulate), down regulate (e.g., inhibit or suppress) or otherwise change a quality of such property, activity, or process. In certain instances, such regulation may be contingent on the occurrence of a specific event, such as activation of a signal transduction pathway, and/or may be manifest only in particular cell types.

As used herein, “specific binding” refers to the ability of a chemically modified tsRNA to bind to a predetermined target. Typically, an chemically modified tsRNA specifically binds to its target with an affinity corresponding to a $K_D$ of about $10^{-7}$ M or less, about $10^{-8}$ M or less, or about $10^{-9}$ M or less and binds to the target with a $K_D$ that is significantly less (e.g., at least 2 fold less, at least 5 fold less, at least 10 fold less, at least 50 fold less, at least 100 fold less, at least 500 fold less, or at least 1000 fold less) than its affinity for binding to a non-specific and unrelated target (e.g., BSA, casein, or an unrelated cell, such as an HEK 293 cell or an *E. coli* cell).

The terms “polynucleotide” and “nucleic acid” are used herein interchangeably. They refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, synthetic polynucleotides, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified, such as by conjugation with a labeling component.

Chemically Modified tsRNAs

In certain aspects, provided herein are chemically-modified RNAs that selectively target pathogenic bacteria (e.g., *Fusobacterium nucleatum*) and/or selectively induces RNA-mediated growth inhibition and/or cell death. In some aspects, provided herein are pharmaceutical compositions comprising such chemically-modified RNAs, methods of using such chemically-modified RNAs to treat pathogenic bacteria-associated disease (e.g., periodontal diseases, preterm birth issues and colorectal cancer) and/or to kill pathogenic bacteria.

In certain aspects, provided herein are chemically modified tsRNAs comprising a nucleic acid sequence that is at least 60% identical (e.g., at least 65% identical, at least 70% identical, at least 75% identical, at least 80% identical, at least 85% identical, at least 90% identical, at least 92% identical, at least 94% identical, at least 96% identical, at least 98% identical) to SEQ ID NO 1 or 2. In certain embodiments, the chemically modified tsRNAs comprise at least 15 (e.g., at least 15, at least 16, at least 17, at least 18, at least 19, at least 20, at least 21, at least 22, at least 23, at least 24, at least 25, at least 26, at least 27) consecutive nucleotides of SEQ ID NO 1 or 2. In some embodiments, the chemically modified tsRNAs comprise a nucleic acid sequence of SEQ ID NO 1 or 2. In some embodiments, the chemically modified tsRNAs provided herein have a sequence consisting essentially of SEQ ID NO 1 or 2. In certain embodiments, the chemically modified tsRNAs provided herein have a sequence consisting of SEQ ID NO 1 or 2.

In certain embodiments, the chemically modified tsRNAs provided herein are no more than 60 nucleotides in length (e.g., no more than 60 nucleotides in length, no more than 55 nucleotides in length, no more than 50 nucleotides in length, no more than 45 nucleotides in length, no more than 40 nucleotides in length, no more than 35 nucleotides in length, no more than 34 nucleotides in length, no more than 33 nucleotides in length, no more than 32 nucleotides in length, no more than 31 nucleotides in length, no more than 30 nucleotides in length, or no more than 29 nucleotides in length).

In some embodiments, the chemically modified tsRNAs provided herein are able to inhibit growth of *F. nucleatum*. In some embodiments, the chemically modified tsRNAs provided herein are able to induce death of *F. nucleatum*. In some embodiments, the chemically modified tsRNAs inhibit growth and/or induce cell death of *F. nucleatum* in vitro. In certain embodiments, the chemically modified tsRNAs inhibit growth and/or induce cell death of *F. nucleatum* in vivo (e.g., in a human and/or an animal model).

In some embodiments, the chemically modified tsRNAs provided herein comprise one or more chemical modifications. In some embodiments, the chemically modified tsRNAs comprise one or more (e.g., at least 1, 2, 3, 4, 5, 6, 7, 8, 9, 10 11, 12, 13, 14, 15, 16, 17, 18, 19, 20, 21, 22, 23, 24, 25, or 26) 2' sugar substitutions (e.g. a 2'-fluoro, a 2'-amino, or a 2'-O-methyl substitution). In some embodiments, the chemically modified tsRNA comprises at least one (e.g., 1, 2, 3, 4, 5, 6, 7, 8, 9, 10 11, 12, or 13) 2'-O-methylated nucleotide positioned at the 3' end. In certain embodiments, the chemically modified tsRNA comprises one, two, or three consecutive 2'-O-methylated nucleotides positioned at the 3' end. In some embodiments, the chemically modified tsRNA comprises at least one (e.g., 1, 2, 3, 4, 5, 6, 7, 8, 9, 10 11, 12, or 13) 2'-O-methylated nucleotide positioned at the 5' end. In certain embodiments, the chemically modified tsRNA comprises one, two, or three consecutive 2'-O-methylated nucleotides positioned at the 3' end. In certain embodiments, the chemically modified tsRNA comprises one, two, or three consecutive 2'-O-methylated nucleotides positioned at the 5' end. In specific embodiments, the chemically modified tsRNA comprises three consecutive 2'-O-methylated nucleotides positioned at the 5' end and three consecutive 2'-O-methylated nucleotides positioned at the 3' end. In some embodiments, not all nucleotides of the chemically modified tsRNA are 2'-O-methylated.

In some embodiments, the chemically modified tsRNAs comprise one or more (e.g., at least 1, 2, 3, 4, 5, 6, 7, 8, 9, 10 11, 12, 13, 14, 15, 16, 17, 18, 19, 20, 21, 22, 23, 24, 25, or 26) phosphorothioate internucleotide bonds. In some embodiments, the chemically modified tsRNA comprises at least one (e.g., 1, 2, 3, 4, 5, 6, 7, 8, 9, 10 11, 12, or 13) phosphorothioate internucleotide bond at the 3' end. In some embodiments, the chemically modified tsRNA comprises at least one (e.g., 1, 2, 3, 4, 5, 6, 7, 8, 9, 10 11, 12, or 13) phosphorothioate internucleotide bond at the 5' end. In certain embodiments, the chemically modified tsRNA comprises one or two consecutive phosphorothioate internucleotide bonds at the 3' end. In certain embodiments, the chemically modified tsRNA comprises one or two consecutive phosphorothioate internucleotide bonds at the 5' end. In specific embodiments, the chemically modified tsRNA comprises two consecutive phosphorothioate internucleotide bonds at the 5' end and two consecutive phosphorothioate internucleotide bonds at the 3' end.

In some embodiments, chemically modified tsRNA comprises three consecutive 2'-O-methylated nucleotides positioned at the 5' end, three consecutive 2'-O-methylated nucleotides positioned at the 3' end, two consecutive phosphorothioate internucleotide bonds at the 3' end, and two consecutive phosphorothioate internucleotide bonds at the 5' end. In specific embodiments, the chemically modified tsRNA is AS38 or AS39.

In some embodiments, the chemically modified tsRNA has an increased stability compared to a naturally occurring tsRNA with the same sequence. In specific embodiments, the chemically modified tsRNA increases growth inhibition of *Fusobacterium nucleatum* (Fn) by at least 1.2-fold, at least 1.5-fold, at least 1.8-fold, at least 2-fold, at least 2.2-fold, at least 2.5-fold, at least 2.8-fold, at least 3-fold, at least 3.2-fold, at least 3.5-fold, at least 3.8-fold, at least 4-fold, at least 4.2-fold, at least 4.5-fold, at least 4.8-fold, at least 5-fold, at least 5.2-fold, at least 5.5-fold, at least 5.8-fold, at least 6-fold, at least 6.2-fold, at least 6.5-fold, at least 6.8-fold, at least 7-fold, at least 7.2-fold, at least 7.5-fold, at least 7.8-fold, at least 8-fold, at least 8.2-fold, at least 8.5-fold, at least 8.8-fold, at least 9-fold, at least 9.2-fold, at least 9.5-fold, at least 9.8-fold, at least 10-fold, at least 10.5-fold, at least 11-fold, at least 12-fold, at least 13-fold, at least 14-fold, at least 15-fold, at least 20-fold, at least 25-fold, at least 30-fold, at least 35-fold, at least 40-fold, at least 45-fold, at least 50-fold, at least 60-fold, at least 70-fold, at least 80-fold, at least 90-fold, or at least 100-fold.

In some embodiments, the chemically modified tsRNA increases growth inhibition of *Fusobacterium nucleatum* (Fn) compared to a naturally occurring tsRNA with the same sequence. In specific embodiments, the chemically modified tsRNA increases growth inhibition of *Fusobacterium nucleatum* (Fn) by at least at least 50-fold, at least 60-fold, at least 70-fold, at least 80-fold, at least 90-fold, at least 100-fold, at least 200-fold, at least 300-fold, at least 400-fold, at least 500-fold, at least 600-fold, at least 700-fold, at least 800-fold, at least 900-fold, at least 1000 fold, at least 1100-fold, at least 1200-fold, at least 1300-fold, at least 1400-fold, at least 1500-fold, at least 1600-fold, at least 1700-fold, at least 1800-fold, at least 1900-fold, at least 2000-fold, at least 2500 fold, at least 3000 fold, at least 3500 fold, at least 4000 fold, at least 4500 fold, at least 5000 fold, at least 5500 fold, at least 6000-fold, at least 6500 fold, at least 7000 fold, at least 7500 fold, at least 8000 fold, at least 8500 fold, at least 9000 fold, at least 9500 fold, or at least 10000 fold.

Pharmaceutical Compositions

In certain aspects, provided herein are pharmaceutical compositions comprising at least one chemically modified tsRNA (e.g., a therapeutically effective amount of a chemically modified tsRNA) provided herein. In some embodiments, the pharmaceutical compositions provided herein comprise two chemically modified tsRNAs: one is selected from AS38 and AS41, and the other one is selected from AS39 and AS42. In some embodiments, the pharmaceutical compositions provided herein comprise two chemically modified tsRNAs: AS38 and AS39. In some embodiments, the pharmaceutical compositions provided herein comprise two chemically modified tsRNAs: AS41 and AS42. In some embodiments, the pharmaceutical compositions provided herein further comprise a pharmaceutically acceptable carrier. In some embodiments, the pharmaceutical compositions provided herein are formulated for parenteral administration. (e.g., subcutaneous administration).

In certain embodiments, the pharmaceutical compositions provided herein are for use in treating *F. nucleatum* infection. In certain embodiments, the pharmaceutical compositions provided herein are for use in treating *F. nucleatum*-associated disease. In some embodiments, the *F. nucleatum*-associated disease is a periodontal disease. In some embodiments, the *F. nucleatum*-associated disease is a preterm birth issue. In some embodiments, the *F. nucleatum*-associated disease is a colorectal cancer.

"Pharmaceutically acceptable carrier" refers to a substance that aids the administration of an active agent to and absorption by a subject and can be included in the compositions described herein without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylase or starch, fatty acid esters, hydroxymethy cellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compositions described herein. One of skill in the art will recognize that other pharmaceutical excipients are useful.

Therapeutic Methods

In some aspects, provided herein are methods of treating *F. nucleatum* infection comprising the administration of a pharmaceutical composition comprising one or more chemically modified tsRNAs provided herein.

In some aspects, provided herein are methods of treating a *F. nucleatum*-associated disease comprising the administration of a pharmaceutical composition comprising one or more chemically modified tsRNAs provided herein.

In some embodiments, the *F. nucleatum*-associated disease is a periodontal disease. In some embodiments, the *F. nucleatum*-associated disease is a preterm birth issue. In some embodiments, the *F. nucleatum*-associated disease is a colorectal cancer. In some embodiment, the method comprising administering to the subject two chemically modified tsRNAs: one is selected from AS38 and AS41, and the other one is selected from AS39 and AS42 (e.g., the combination of AS38 and AS39, or the combination of AS41 and AS42). In some embodiments, the chemically modified tsRNA or the pharmaceutical composition is administered in a pharmaceutically acceptable formulation. In some embodiments, the administration is parenteral administration (e.g., subcutaneous administration). In some embodiments, the subject is a human. Thus, in certain aspects, provided herein is a method of delivering a chemically modified tsRNA and/or a pharmaceutical composition described herein to a subject.

In certain embodiments, the pharmaceutical compositions and chemically modified tsRNAs described herein can be administered in conjunction with any other conventional treatment treating *Fusobacterium nucleatum* infection, such as antibiotics or other inhibitors that reduces growth or induce death of *Fusobacterium nucleatum*. In certain embodiments, the pharmaceutical compositions and chemically modified tsRNAs described herein can be administered in conjunction with any other conventional treatment for treating *Fusobacterium nucleatum*-associated periodontal diseases. In certain embodiments, the pharmaceutical compositions and chemically modified tsRNAs described herein can be administered in conjunction with any other conventional treatment for treating *Fusobacterium nucleatum*-associated preterm birth issues. In certain embodiments, the pharmaceutical compositions and chemically modified tsRNAs described herein can be administered in conjunction with anti-cancer treatment for treating *Fusobacterium nucleatum*-associated colorectal cancer. Such anti-cancer treatment include, for example, radiation therapy and surgical resection of the tumor. These treatments may be applied as necessary and/or as indicated and may occur before, concurrent with or after administration of the pharmaceutical compositions, chemically modified tsRNAs, dosage forms, and kits described herein.

In certain embodiments, the method comprises the administration of multiple doses of the chemically modified tsRNA or the pharmaceutical compositions. Separate administrations can include any number of two or more administrations (e.g., doses), including 2, 3, 4, 5, 6, 7, 8, 9, 10, 11, 12, 13, 14, 15, 16, 20, 21, 22, 23, 24, or 25 administrations. One skilled in the art can readily determine the number of administrations to perform, or the desirability of performing one or more additional administrations, according to methods known in the art for monitoring therapeutic methods and other monitoring methods provided herein. Accordingly, the methods provided herein include methods of providing to the subject one or more administrations of an chemically modified tsRNA and/or a pharmaceutical composition described herein, where the number of administrations can be determined by monitoring the subject, and, based on the results of the monitoring, determining whether or not to provide one or more additional administrations. Deciding on whether or not to provide one or more additional administrations can be based on a variety of monitoring results, including, but not limited to, growth and/or viability of *Fusobacterium nucleatum*, indication of bone loss, indication of tumor growth or inhibition of tumor growth, appearance of new metastases or inhibition of metastasis, the overall health of the subject and/or the weight of the subject.

The time period between administrations can be any of a variety of time periods. In some embodiments, the doses may be separated by at least 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 days or 1, 2, 3, or 4 weeks. The time period between administrations can be a function of any of a variety of factors, including monitoring steps, as described in relation to the number of administrations, the time period for a subject to mount a response and/or the time period for a subject to clear the chemically modified tsRNAs from normal tissue. In one example, the time period can be a function of the time period for a subject to mount a response; for example, the time period can be more than the time period for a subject to mount a response, such as more than about one week, more than about ten days, more than about two weeks, or more than about a month; in another example, the time period can be less than the time period for a subject to mount a response, such as less than about one week, less than about ten days, less than about two weeks, or less than about a month. In another example, the time period can be a function of the time period for a subject to clear the chemically modified tsRNAs from normal tissue; for example, the time period can be more than the time period for a subject to clear the chemically modified tsRNAs from normal tissue, such as more than about an hour, more than about a day, more than about two days, more than about three days, more than about five days, or more than about a week; in another example, the time period can be less than the time period for a subject to clear the chemically modified tsRNAs from normal tissue, such as less than about an hour, less than about a day, less than about two days, less than about three days, less than about five days, or less than about a week.

The effective dose of a chemically modified tsRNA described herein is the amount of the chemically modified tsRNA that is effective to achieve the desired therapeutic response for a particular patient, composition, and mode of administration, with the least toxicity to the patient. The effective dosage level can be identified using the methods described herein and depends upon a variety of pharmacokinetic factors including the activity of the particular compositions administered, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts. In general, an effective dose is the amount of the therapeutic agent which is the lowest dose effective to produce a therapeutic effect. Such an effective dose generally depends upon the factors described above.

Examples of routes of administration include oral administration, rectal administration, topical administration, inhalation (nasal) or injection. Administration by injection includes intravenous (IV), intralesional, peritumoral, intramuscular (IM), and subcutaneous (SC) administration. The compositions described herein can be administered in any form by any effective route, including but not limited to oral, parenteral, enteral, intravenous, intratumoral, intraperitoneal, topical, transdermal (e.g., using any standard patch), intradermal, ophthalmic, (intra)nasally, local, non-oral, such as aerosol, inhalation, subcutaneous, intramuscular, buccal, sublingual, (trans)rectal, vaginal, intra-arterial, and intrathecal, transmucosal (e.g., sublingual, lingual, (trans)buccal, (trans)urethral, vaginal (e.g., trans- and perivaginally), implanted, intravesical, intrapulmonary, intraduodenal, intragastrical, and intrabronchial. In some embodiments, the chemically modified tsRNAs described herein are administered orally, rectally, topically, intravesically, by injection into or adjacent to a draining lymph node, intravenously, by inhalation or aerosol, or subcutaneously. In some embodiments, the administration is parenteral administration (e.g., subcutaneous administration).

The dosage regimen can be any of a variety of methods and amounts, and can be determined by one skilled in the art according to known clinical factors. As is known in the medical arts, dosages for any one patient can depend on many factors, including the subject's species, size, body surface area, age, sex, immunocompetence, bacterial load, tumor dimensions, and general health, the particular chemically modified tsRNA to be administered, duration and route of administration, the kind and stage of the disease, and other compounds such as drugs being administered concurrently.

The dose of the pharmaceutical compositions described herein may be appropriately set or adjusted in accordance with the dosage form, the route of administration, the degree or stage of a target disease, and the like.

One skilled in the art will recognize that dosage will depend upon a variety of factors including the strength of the particular compound employed, as well as the age, species, condition, and body weight of the subject. The size of the dose will also be determined by the route, timing, and frequency of administration as well as the existence, nature, and extent of any adverse side-effects that might accompany the administration of a particular compound and the desired physiological effect.

Suitable doses and dosage regimens can be determined by conventional range-finding techniques known to those of ordinary skill in the art. Generally, treatment is initiated with smaller dosages, which are less than the optimum dose of the compound. Thereafter, the dosage is increased by small increments until the optimum effect under the circumstances is reached. An effective dosage and treatment protocol can be determined by routine and conventional means, starting, e.g., with a low dose in laboratory animals and then increasing the dosage while monitoring the effects, and systematically varying the dosage regimen as well. Animal studies are commonly used to determine the maximal tolerable dose ("MTD") of bioactive agent per kilogram weight. Those skilled in the art regularly extrapolate doses for efficacy, while avoiding toxicity, in other species, including humans.

In accordance with the above, in therapeutic applications, the dosages of the chemically modified tsRNAs provided herein may vary depending on the specific chemically modified tsRNA, the age, weight, and clinical condition of the recipient patient, and the experience and judgment of the clinician or practitioner administering the therapy, among other factors affecting the selected dosage. Generally, the dose should be sufficient to result in slowing the growth of, and preferably inducing death of *Fusobacterium nucleatum*.

EXAMPLES

Example 1. TsRNAs Against *F. nucleatum*

Figure 1B:
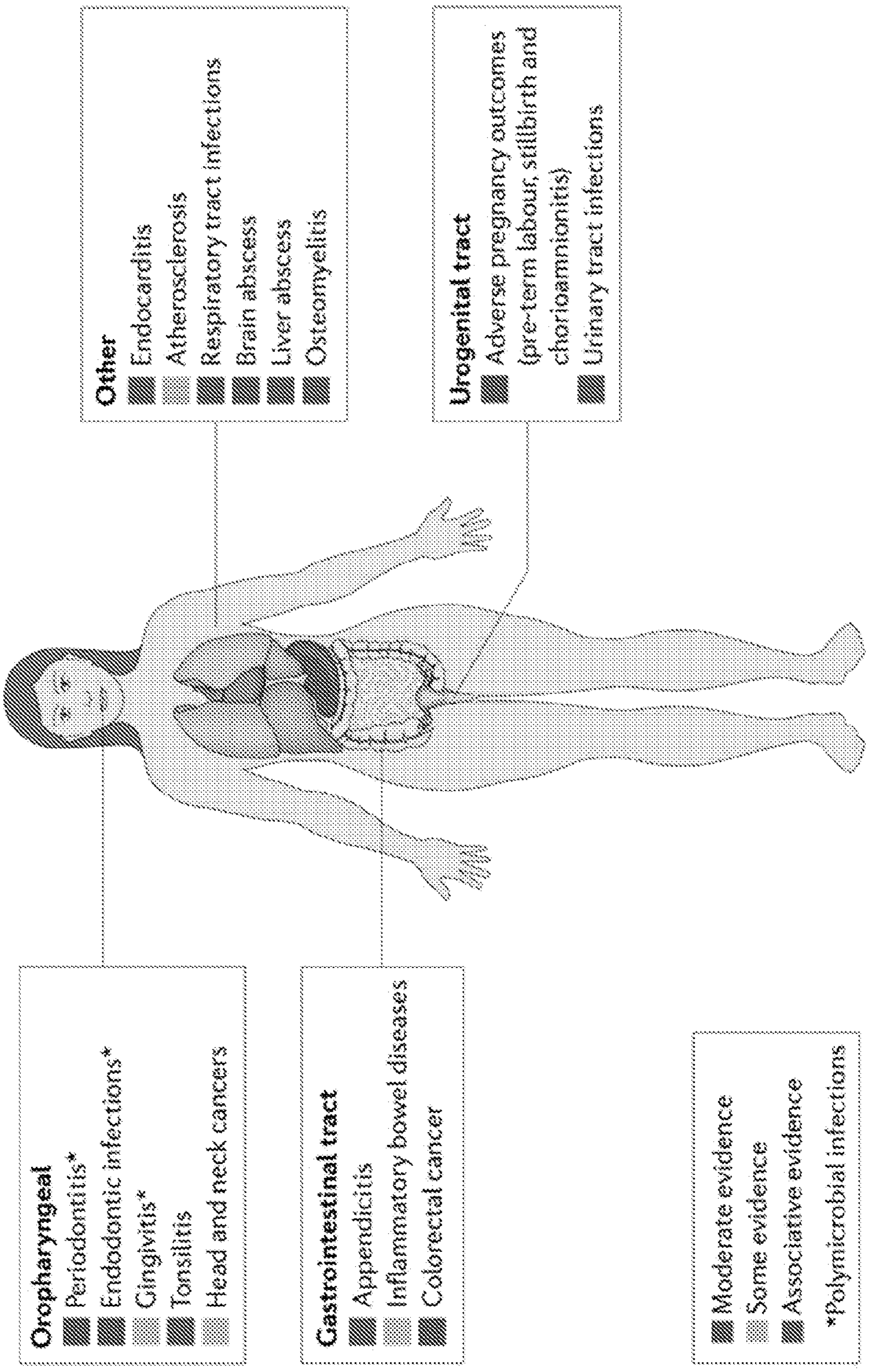
FIG. 1B shows oral and extraoral diseases associated with *Fusobacterium nucleatum* (Fn).

*Fusobacterium nucleatum* is a gram-negative anaerobe ubiquitous to the oral cavity and associated with periodontal disease (FIG. 1A). It is also associated with preterm birth and has been isolated from the amniotic fluid, placenta, and chorioamnionic membranes of women delivering prematurely. Moreover, the presence of *Fusobacterium nucleatum* highly correlates with the incidence of colorectal cancer. Increasing lines of evidence showed that *Fusobacterium nucleatum* contributes to the carcinogesis of colorectal cancer by inducing inflammation and suppressing host immunity (FIG. 1B; Brennan and Garrett (2019) *Nat. Rev. Microbio.* 17:156-166).

There is no drug available to specifically target *Fusobacterium nucleatum* but spare normal and health-associated bacteria. Antibiotics can be used to eliminate *Fusobacterium nucleatum* but also kill health-associated bacteria. Therefore usage of antibiotics to treat diseases associated with *Fusobacterium nucleatum* can cause dysbiosis.

Transfer RNA (tRNA)-derived small sRNA (tsRNA) can be classified into two types: (1) the 5' and 3' tRNA halves are 30-40 nt long and are produced by cleavage of mature cytoplasmic tRNAs; and (2) the shorter tRNA-derived fragments (tRFs) are 18-22 nt long, and are produced from both mature and pre-tRNAs by Dicer or RNase Z. Endogenous tsRNAs can modulate cellular growth. For example, archaea-derived tsRNAs can inhibit bacterial and eukaryotic protein biosynthesis. It has been shown that human host generated transfer RNA-derived small sRNA (tsRNA)-tsRNA-000794 and tsRNA-020498 induced growth inhibition in *Fusobacterium nucleatum* (*F. nucleatum*) at micromolar range (FIGS. 2A-2E).

```
tsRNA-000794:
                                        (SEQ ID NO: 1)
5'- CCGGCUAGCUCAGUCGGUAGAGCAUGAG[mA]-3'

tsRNA-020498:
                                        (SEQ ID NO: 2)
5'- GGGGGUAUAGCUCAGUGGGUAGAGCA[mU]-3'
```

[m]: refers to methylation at the 2'OH of the nucleotide

Figure 2B:
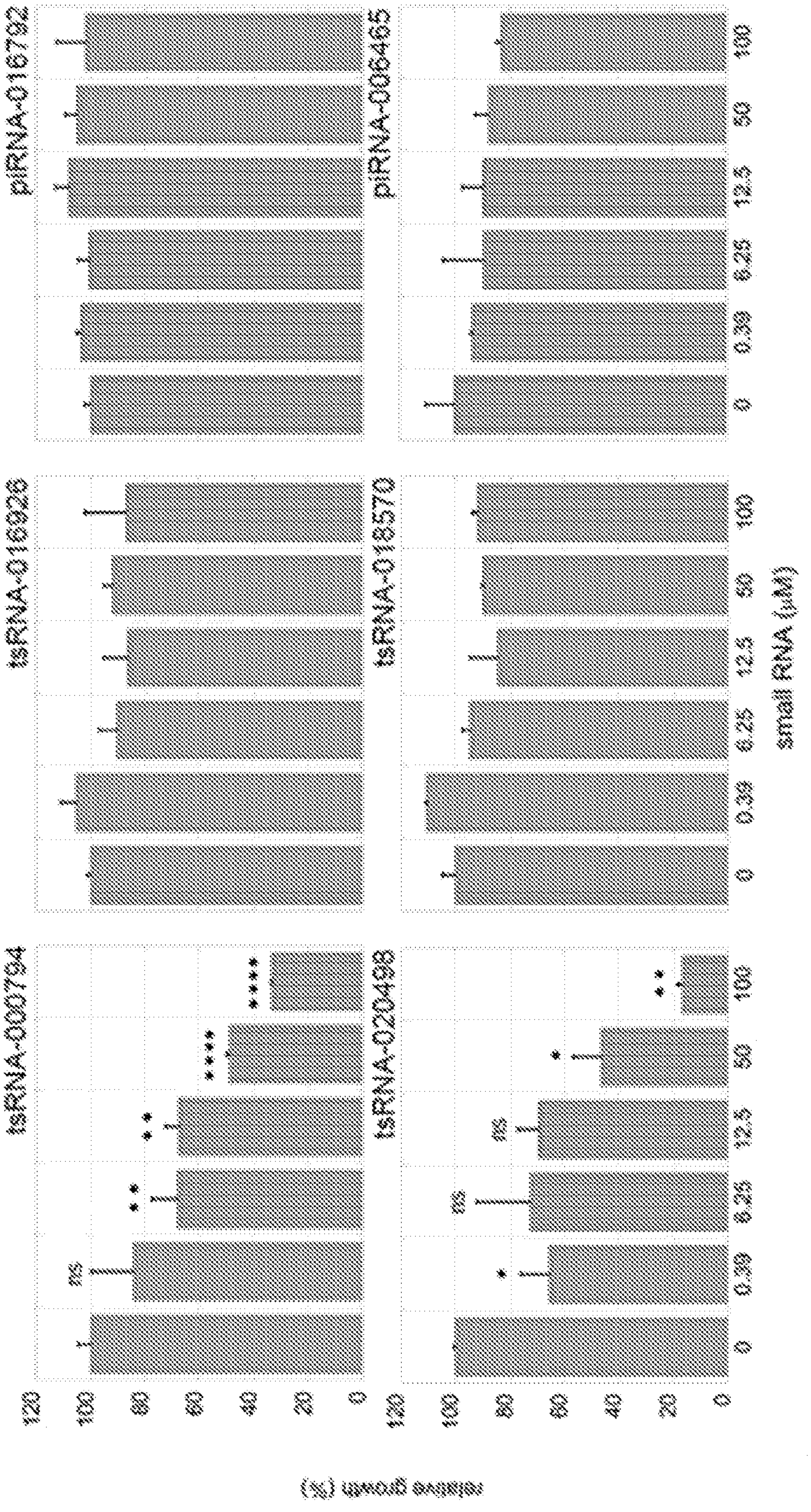
FIGS. 2B-2E show that the two naturally occurring tsRNA-000794 and tsRNA-020498 (hereinafter AS41 and AS42, respectively) induced growth inhibition in *Fusobacterium nucleatum*.
Figure 2C:
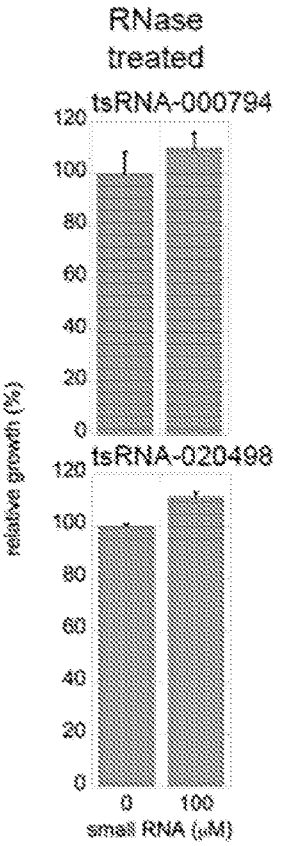
Figure 2D:
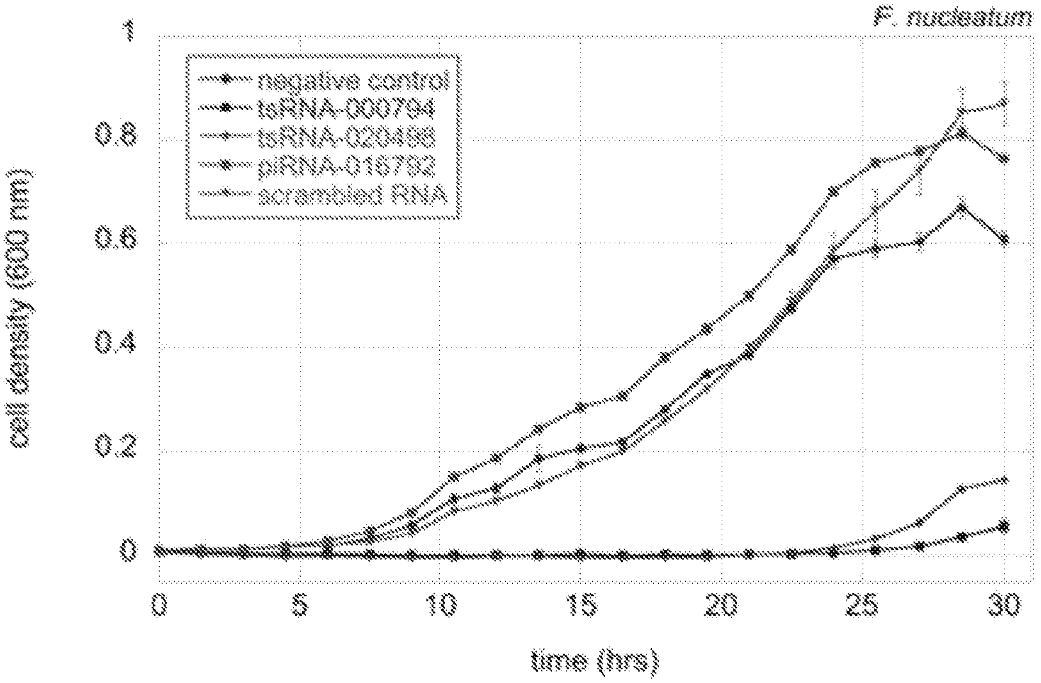
Figure 2E:
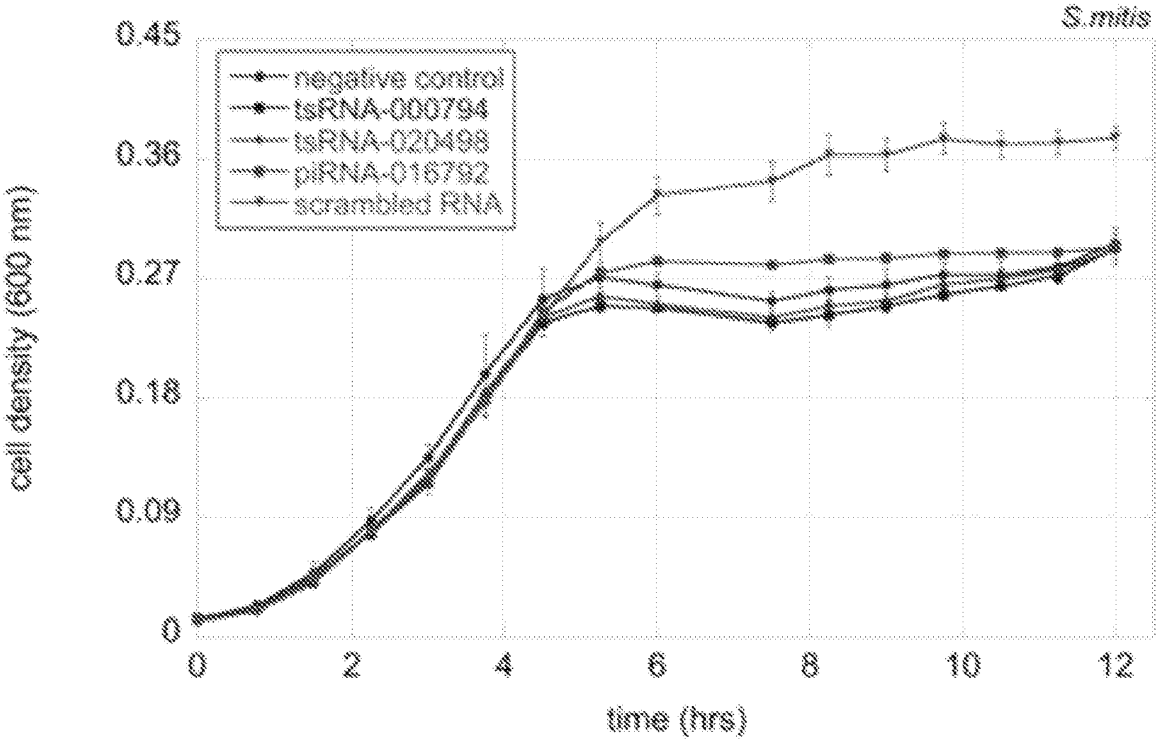

In salivary exosomes from healthy human subjects, two host-derived tsRNAs, tsRNA-000794 and tsRNA-020498 were identified (FIG. 2A). These tsRNAs exist at a nanomolar range in saliva (preliminary data, not shown) and bear high sequence similarity to specific endogenous transfer RNAs (tRNAs) from Fn. It was further shown that human Normal Oral Keratinocyte-Spontaneously Immortalized (NOKSI) cells release these two specific tsRNAs encapsulated in exosomes in response to the presence of Fn. Importantly, these two tsRNAs display selective antimicrobial activity—chemically synthesized tsRNA-000794 and tsRNA-020498 inhibited the growth of Fn in liquid culture, but not that of *Streptococcus mitis* (Sm), a health-associated gram-positive oral bacterium (FIGS. 2B-2E). Additional description can be found in He et al. (2018) *Journal of Dental Research* 97(11):1236-1243, the content of which is incorporated by reference herein in its entirety. However, these naturally occurring tsRNAs require micromolar concentration to achieve inhibitory effect against Fn.

Example 2. Targeted Chemical Modifications Lead to Over 1000-Fold Increase in Antimicrobial Efficacy of tsRNAs Against *F. nucleatum* (Termed Fn-Targeting tsRNAs)

Chemically modified guide RNAs have been shown previously (Hendel A. et al. (2015) *Nat. Biotechnol.* 33(9):985-989). Different modifications on Fn-targeting tsRNAs have been tested. It was found that the tsRNAs with the 2'-O-methylation at three 5' and 3' terminal nucleotides along with two PS bonds showed the best efficacy and selectivity in inhibiting Fn. A list of chemically modified and naturally occurring tsRNAs used in the study were shown in FIG. 3 and Table 1.

TABLE 1

Chemically modified tsRNA (partial) of tsRNA-000794 and tsRNA-020498

| | | |
|---|---|---|
| tsRNA-000794-MOD (AS38) | tsRNA-000794 (three 2'-OMe and 2PS) | [mC]*[mC]*[mG]GCUAGCUCAGUCG GUAGAGCAUG[mA]*[mG]*[mA] (SEQ ID NO: 3) |
| tsRNA-020498-MOD (AS39) | tsRNA-020498 (three 2'-OMe and 2PS) | [mG]*[mG]*[mG]GGUAUAGCUCAGU GGGUAGAG[mC]*[mA]*[mU] (SEQ ID NO: 4) |
| tsRNA-scramble-MOD (AS40) | scramble RNA (three 2'-OMe and 2PS) | [mG]*[mG]*[mA]CGACAAGUUCGUG ACGAGCGCAU[mC]*[mU]*[mG] (SEQ ID NO: 5) |

*: Phosphorothioate linkage (PS bond)
m: 2'-O-methyl (2'OMe)

Figure 4A:
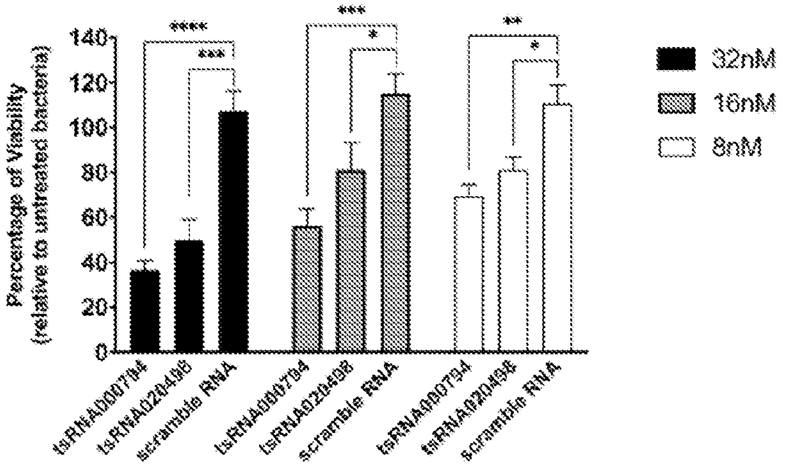
FIGS. 4A-4D show antimicrobial activity of chemically modified tsRNAs against *Fusobacterium nucleatum* subsp. *nucleatum* Knorr (ATCC® 23726™).
Figure 4B:
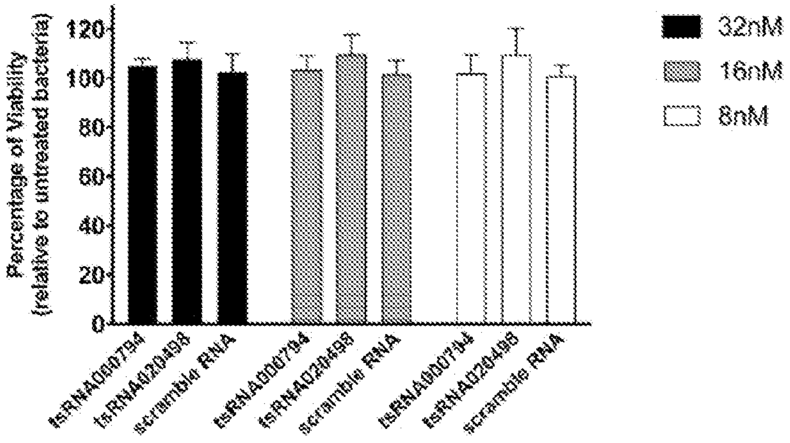
Figure 4C:
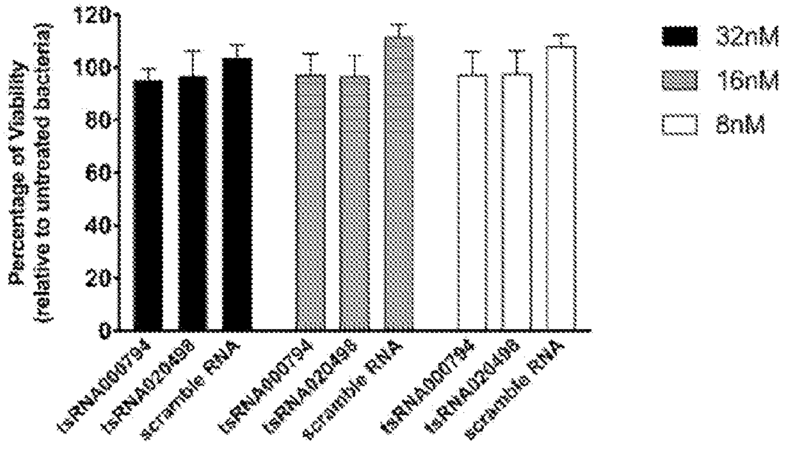
Figure 4D:

*F. nucleatum* were cultured in Columbia broth and incubated at 37° C. under anaerobic conditions (10% $H_2$, 10% $CO_2$, 80% $N_2$) until exponential phase. To test the impact of tsRNAs on bacterial growth dynamics, bacterial cells were seeded in 96-well plates containing 2-time serially diluted tsRNA-000794, tsRNA-020498, or scramble control RNAs, with a starting concentration of $10^6$ CFU/mL. Plates were incubated under anaerobic conditions at 37° C., and $OD_{600}$ was measured with a microplate reader at time intervals indicated in the results. Assays were performed in three independent biological replicates, and mean±SEM values are shown in FIGS. 4A-4C (ns, P>0.05; *P<0.05; P<0.01; *P<0.001). As shown in FIGS. 4A-4C, 2'-O-methylation at three 5' and 3' terminal nucleotides along with two PS bonds resulted in maximal growth inhibition in *F. nucleatum* (FIG. 4A) while both the naturally occurring form which contains a single 2'-O-methylation at the 3' terminus (FIG. 4B), and the full 2'-O-methylation version (FIG. 4C) failed to induce growth inhibition at the same concentrations. FIG. 4D shows the bacterial cultures incubated with specific tsRNAs or PBS control.

Figure 5A:
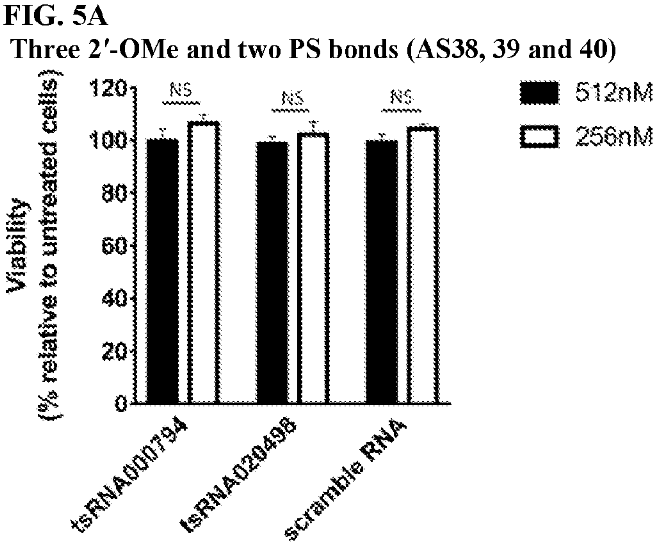
FIGS. 5A-5C show the lack of side effects (cytotoxicity) of chemically modified tsRNAs against an immortalized human oral keratinocyte cell line, NOKSI.
Figure 5B:
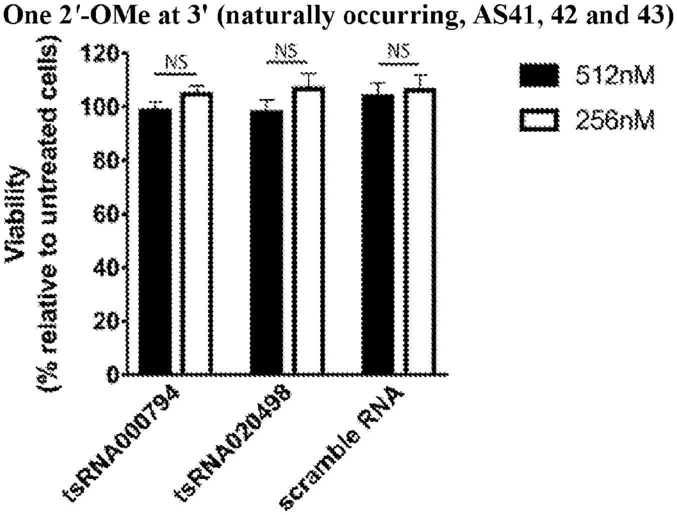
Figure 5C:
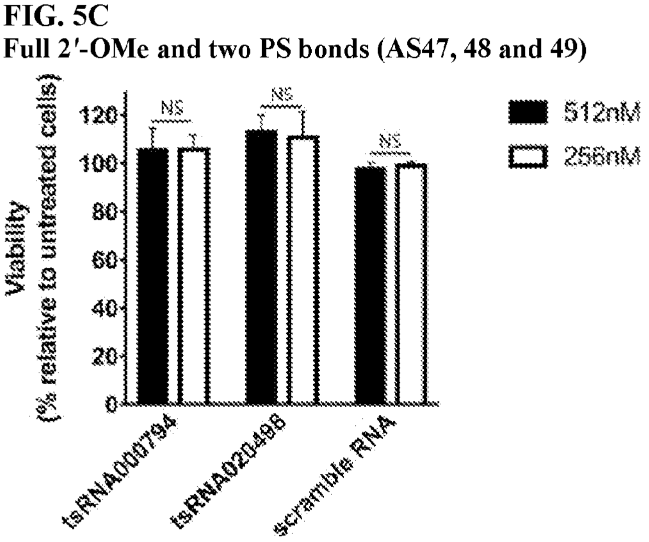
Figure 6A:
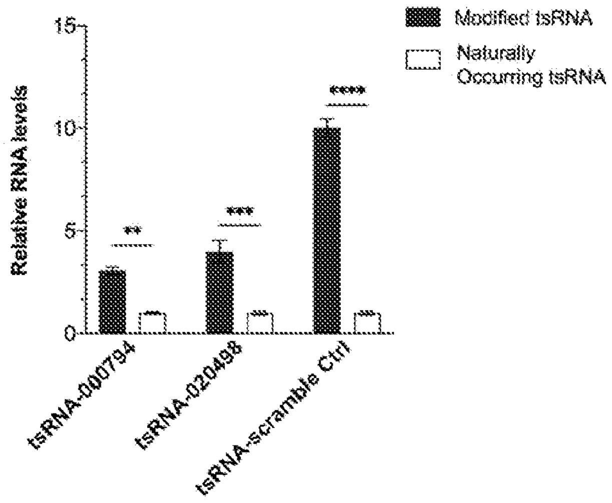
FIGS. 6A-6D show that chemical modifications significantly increased the stability of tsRNAs, and drastically increases the growth inhibition against Fn at nanomolar range, with high specificity (i.e., only targeting Fn).
Figure 6B:
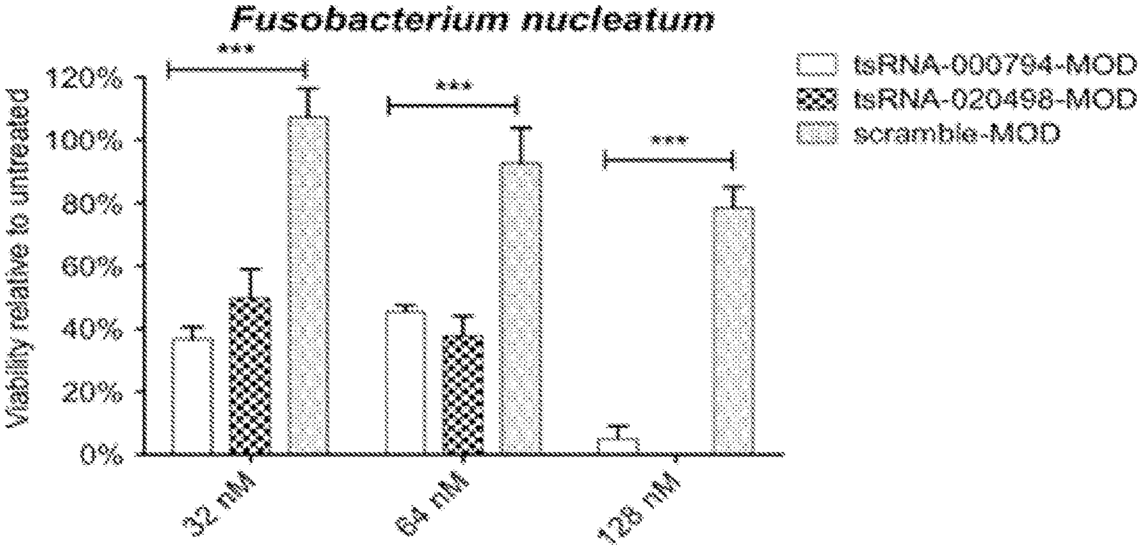
Figure 6C:
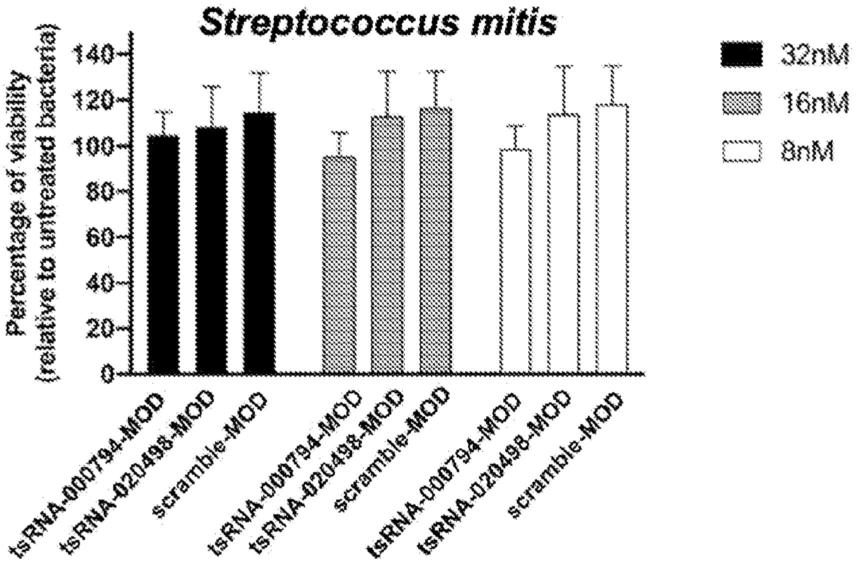
Figure 6D:
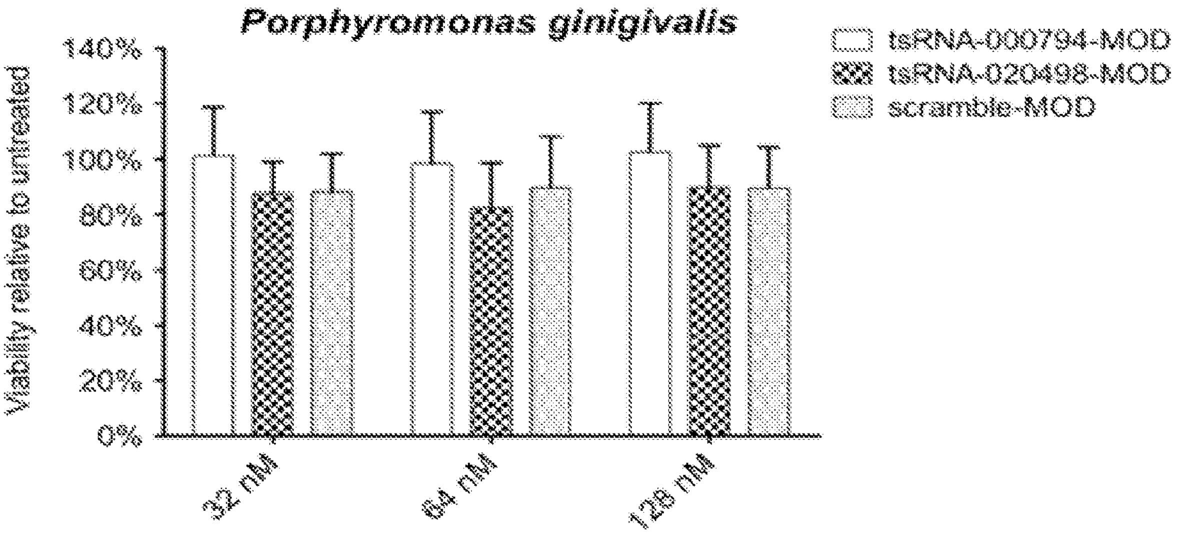

There was lack of side effects (cytotoxicity) of chemically modified tsRNAs against an immortalized human oral keratinocyte cell line, NOKSI. NOKSI cells cultured in defined Keratinocyte serum free media were seeded into 96-well plates and incubated at 37° C. with 5% $CO_2$. After 24 hr, the medium was aspirated and replaced with fresh medium in the presence of tsRNA-000794, tsRNA-020498, or scramble control RNAs of all three different chemical modifications (FIGS. 5A-5C) with concentrations of up to 512 and 256 nM. After 48 hr of incubation with tsRNAs, a MTT cell viability assay was performed. Experiments shown are representative of two biological replicates. FIGS. 5A-5C show that chemically modified tsRNA-000794 and tsRNA-020498 did not reduce viability of NOKSI cells FIGS. 6A-6D show that chemical modifications (2'-O-methylation at three 5' and 3' terminal nucleotides along with two PS bonds) significantly increased the stability of tsRNAs, and drastically increased the growth inhibition against Fn at nanomolar range, with high specificity (i.e., only targeting Fn). FIG. 6A shows that chemical modification (2'-O-methylation at three 5' and 3' terminal nucleotides along with two PS bonds) significantly increased the stability of Fn-targeting tsRNAs. FIG. 6B shows that chemical modified Fn-targeting tsRNAs inhibited *Fusobacterium nucleatum* growth at nanomolar range. FIG. 6C shows that chemical modified Fn-targeting tsRNAs did not inhibit *Streptococcus mitis*, indicating the high specificity. FIG. 6D shows that chemical modified Fn-targeting tsRNAs did not inhibit *Porphyromonas gingivalis*, indicating the high specificity.

Figure 7A:
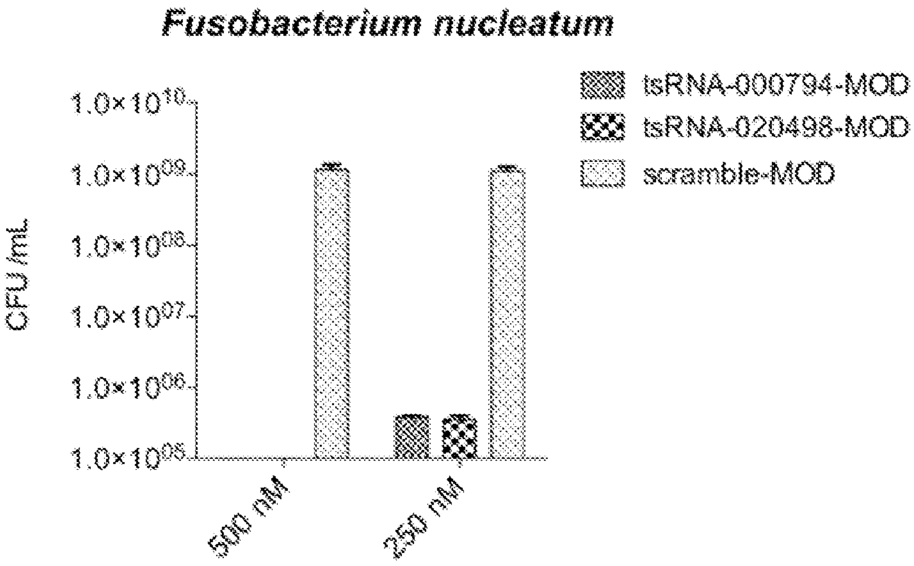
FIGS. 7A-7C show that chemically modified tsRNAs exerted bactericidal effect against *F. nucleatum.*
Figure 7B:
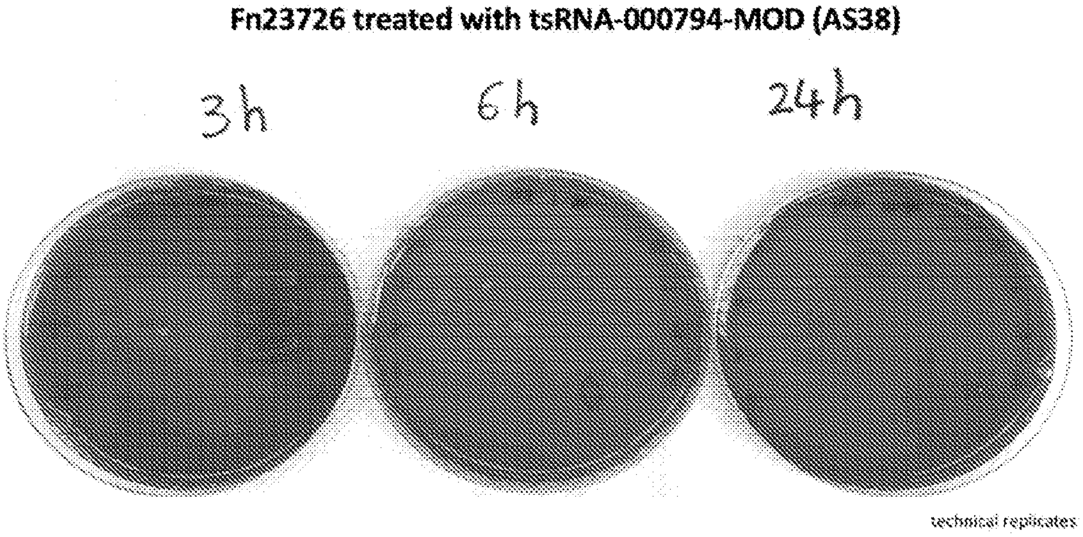
Figure 7C:
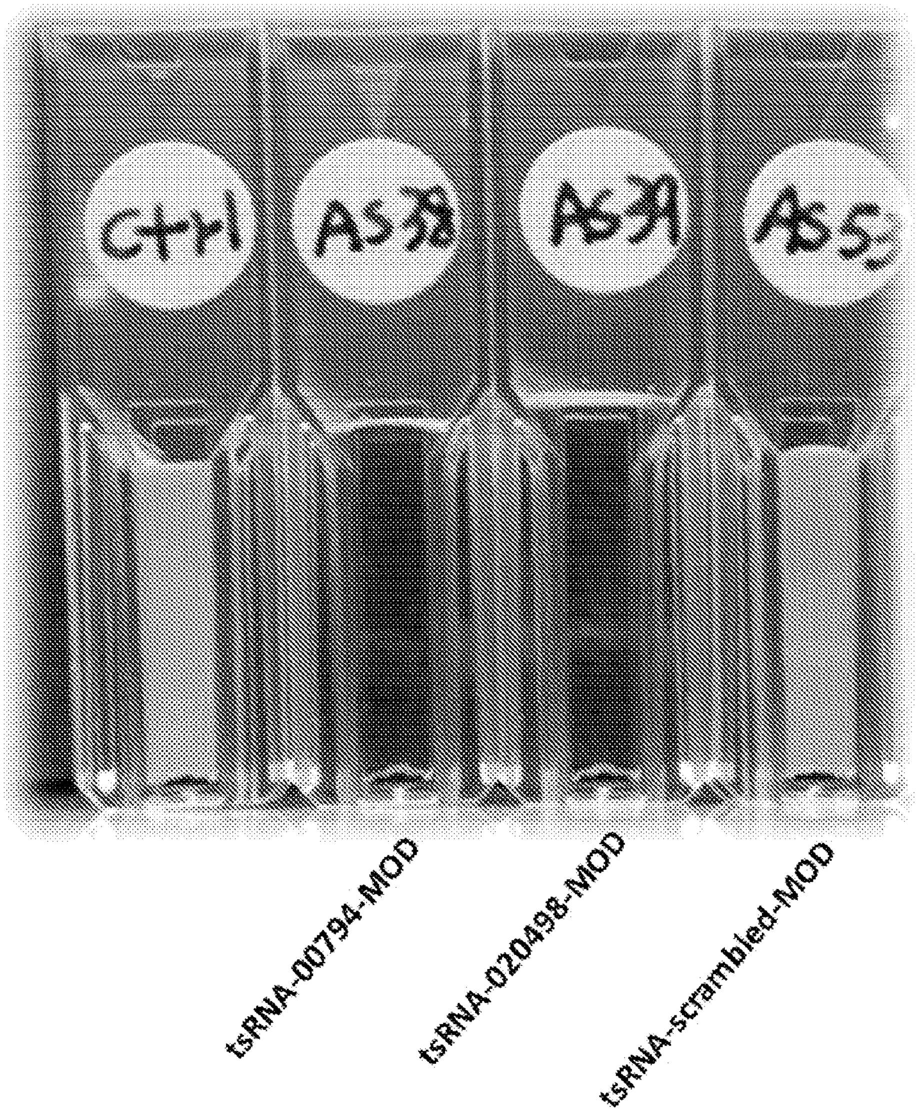

FIGS. 7A-7C show that chemically modified tsRNAs exerted bactericidal (killing) effect against *F. nucleatum.*

There were synergistic effects of two fuso-targeting tsRNAs in *F. nucleatum* subsp. *nucleatum* Knorr (ATCC® 23726TM). *F. nucleatum* were cultured in Columbia broth and incubated at 37° C. under anaerobic conditions (10% $H_2$, 10% $CO_2$, 80% $N_2$) until exponential phase. To test the impact of combined tsRNA on bacterial growth dynamics, bacterial cells were seeded in 96-well plates containing 2-time serially diluted different chemically modified tsRNA-000794 and tsRNA-020498, or the corresponded control tsRNA, with a starting concentration of $10^6$ CFU/mL. Plates were incubated under anaerobic conditions at 37° C., and $OD_{600}$ was measured with a microplate reader at time intervals indicated in the results. Assays were performed in three independent biological replicates, and mean±SEM values are shown in FIGS. 6A and 6B (ns, P>0.05; *P<0.05; P<0.01; *P<0.001).

Figure 8A:
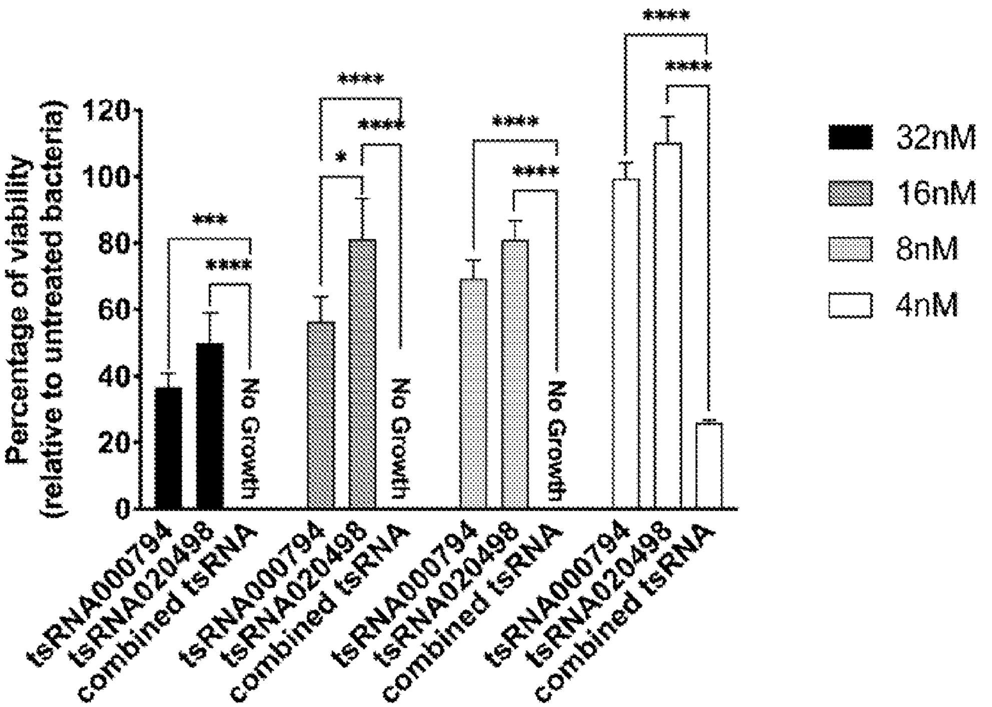
FIGS. 8A and 8B show the synergistic effects of two Fn-targeting tsRNAs in *F. nucleatum* subsp. *nucleatum* Knorr (ATCC® 23726TM).
Figure 8B:
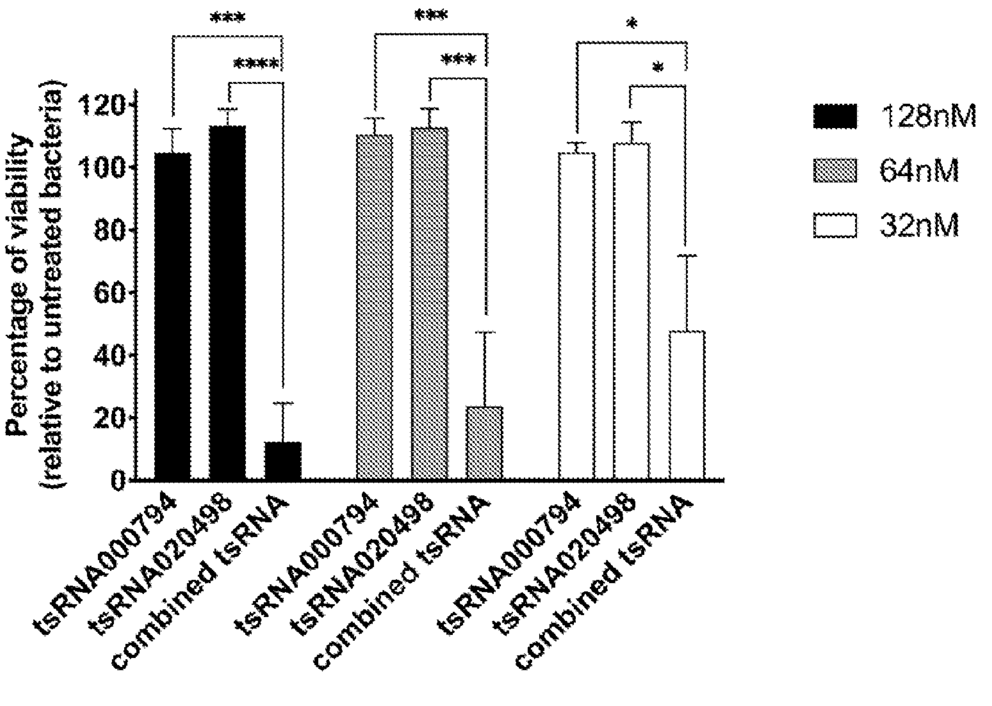

As shown in FIGS. 8A and 8B, combination of two fuso-targeting tsRNAs carrying 2'-O-methylation at three 5' and 3' terminal nucleotides along with two PS bonds demonstrated superior inhibition on the bacterial growth compared to individual tsRNA at the same concentrations. Notably, complete inhibition of bacterial growth was observed when two tsRNAs were added at a concentration as low as 8 nM (FIG. 8A). For naturally occurring Fn-targeting tsRNAs carrying a single 2'-O-methylation at the 3' terminus, they also exhibited the synergistic effect although higher concentrations were required (FIG. 8B). This indicates that two different fuso-targeting tsRNAs can target two different pathways or targets to exert the synergistic growth inhibition A new type of RNA-based "antibiotic" was developed herein to target pathogenic bacteria such as *Fusobacterium nucleatum* and treat *Fusobacterium nucleatum*-associated diseases including periodontal diseases, preterm birth issues and colorectal cancer. Moreover, by multiplexing different small RNAs that target the same pathogenic bacteria, the chance of developing drug-resistant bacteria can be greatly reduced.

In comparison to naturally occurring sRNAs specific for targeting pathogenic bacteria, chemically modified small RNA mimics induced ~1000-fold enhancement in growth inhibition of *Fusobacterium nucleatum*, a key commensal and opportunistic pathogen contributing to periodontitis and colorectal cancer. In contrast, the same RNA mimics did not interfere with growth of *Streptococcus mitis*, a health-associated gram-positive oral bacterium, or *Porphyromonas gingivalis*, a gram-negative oral bacterium, or *E. coli*, a non-oral gram-negative bacterium, indicating its high specificity against *Fusobacterium nucleatum*. While chemically modified tsRNAs are being broadly used for genome editing and RNA interference, it is demonstrated herein to use chemically modified tsRNAs to deal with infectious diseases. Of note, extensive chemical modifications are known to greatly improve RNA stability and pharmacokinetics but at the cost of loss of biological activity. Therefore, chemical modification of RNA requires rational design. The present invention exemplified three areas to enhance the potency of small RNAs as a new therapeutic modality against bacterial infection: (1) different RNA chemical modifications including 2-O-methylation, 3' phosphorothioate and 2' Fluoro; (2) different degrees of modifications in combination with naturally occurring RNA bases; and (3) positions of RNA base modification. This invention can pave way for a new type of antibiotics to address bacterial infection in health.

It was found that modifying the three terminal nucleotides at 5' and 3' reduced the $IC_{50}$ by nearly 1000 times. Other chemical modifications to the RNA backbone without compromising the inhibition efficacy and target specificity are investigated. In addition to 2'-O-methylation, other existing RNA chemistry including 2' fluoride, 2'-O-MOE and LNA are studied. Notably, it is hypothesized that if the tsRNAs directly target proteins, substitution of the 2'-OH with fluoride may reduce potential steric hindrance posed by 2'-O-methylation. Therefore, Fn-targeting tsRNAs having modifications with 2' fluoride and/or 2'-O-MOE are also contemplated.

Figure 9A:
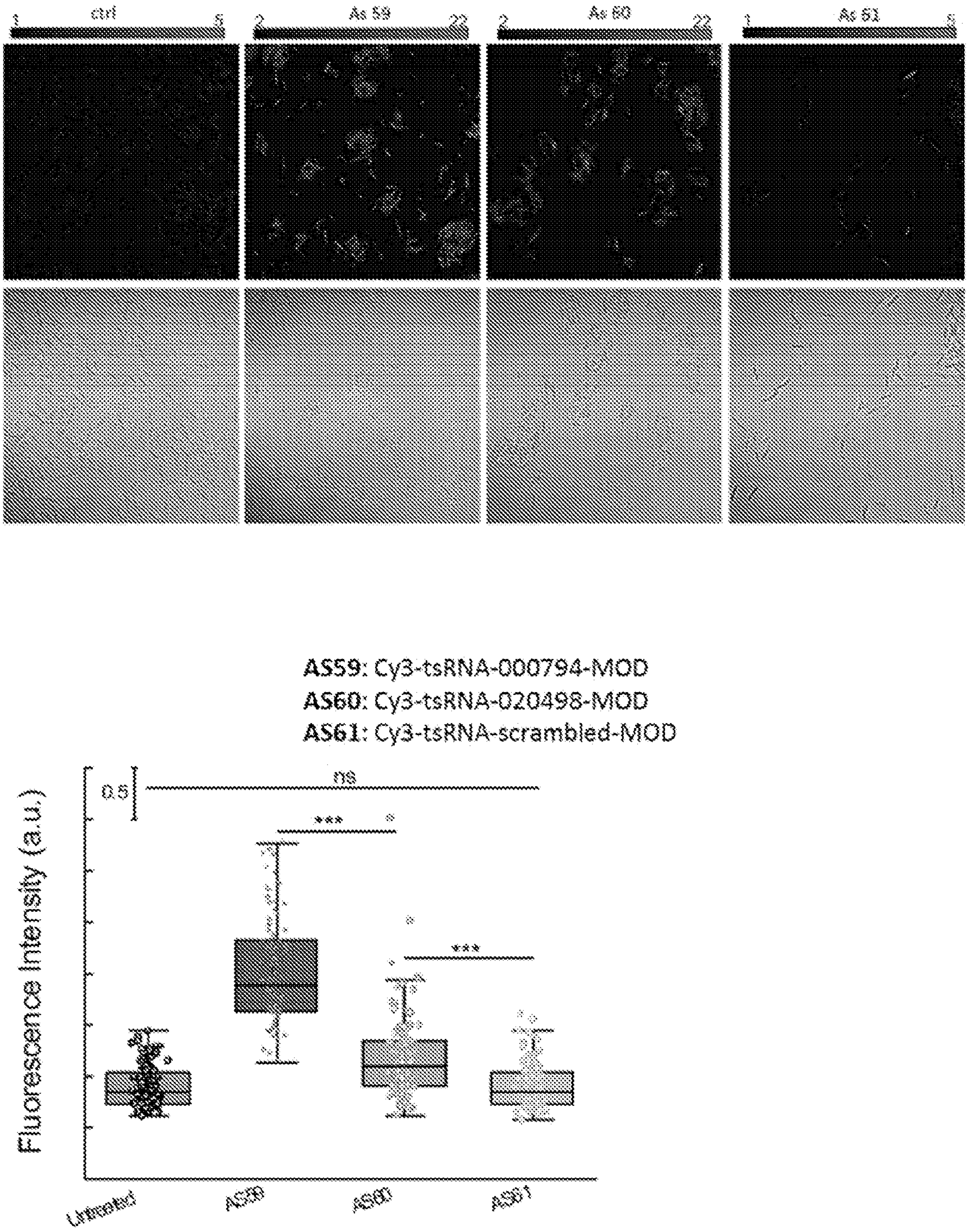
FIGS. 9A-9C show internalization of Fn-targeting tsRNAs by *Fusobacterium nucleatum* (Fn23726), but not *Streptococcus mitis*.
Figure 9B:
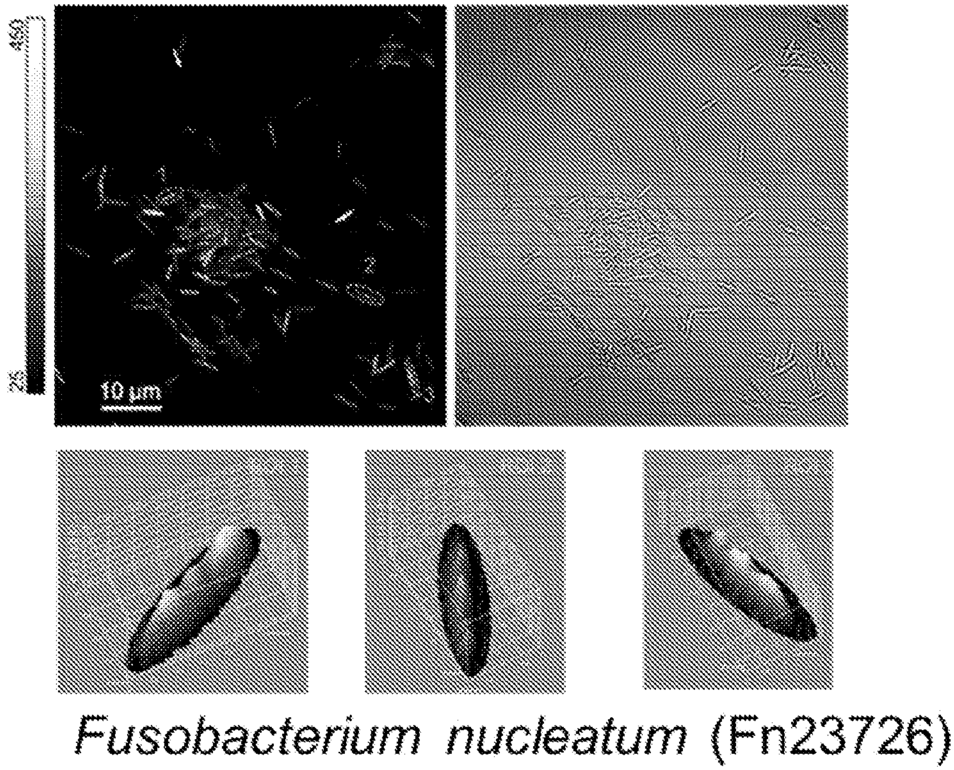
Figure 9C:
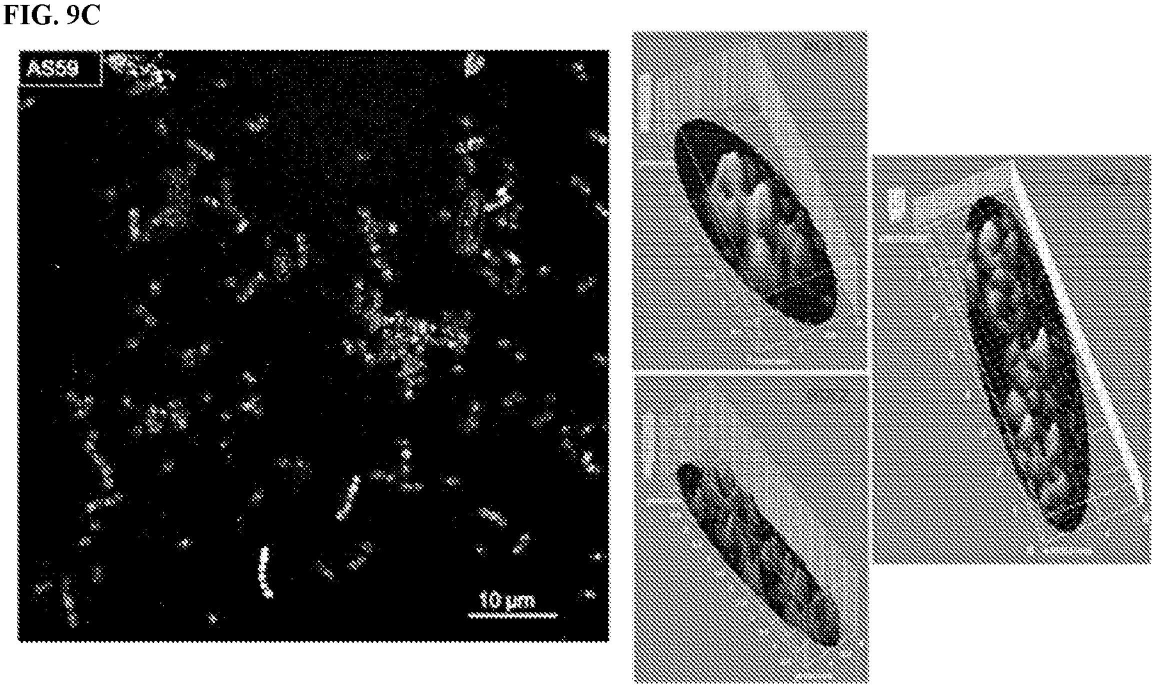

Example 3. Internalization of Fn-Targeting tsRNAs by Multiple *Fusobacterium nucleatum* (Fn) Species It was next demonstrated that Fn-targeting tsRNAs can be uptaken by Fn cells. FIGS. 9A-9C show that Cy3 labeled tsRNA uptake by *Fusobacterium nucleatum* strain 23726, but not *Streptococcus mitis*. FIG. 9A shows that Fn 23726 uptook more Cy3-labeled tsRNA-000794-MOD which is consistent with the best killing effect of the modified tsRNA-000794. Quantitative analysis of the fluorescence intensity was performed by student unpaired t-test. FIG. 9B shows confocal imaging (Airyscan) of the uptake of the Cy3-labeled tsRNA-000794 by Fn 23726 by showing the signal of tsRNAs accumulated in the cytoplasm. FIG. 9C shows confocal imaging (Airyscan) which shows that in the case of *Streptococcus mitis*, tsRNA was accumulated in the cell membrane area as granules, but not inside of the cytoplasm.

Figure 10:
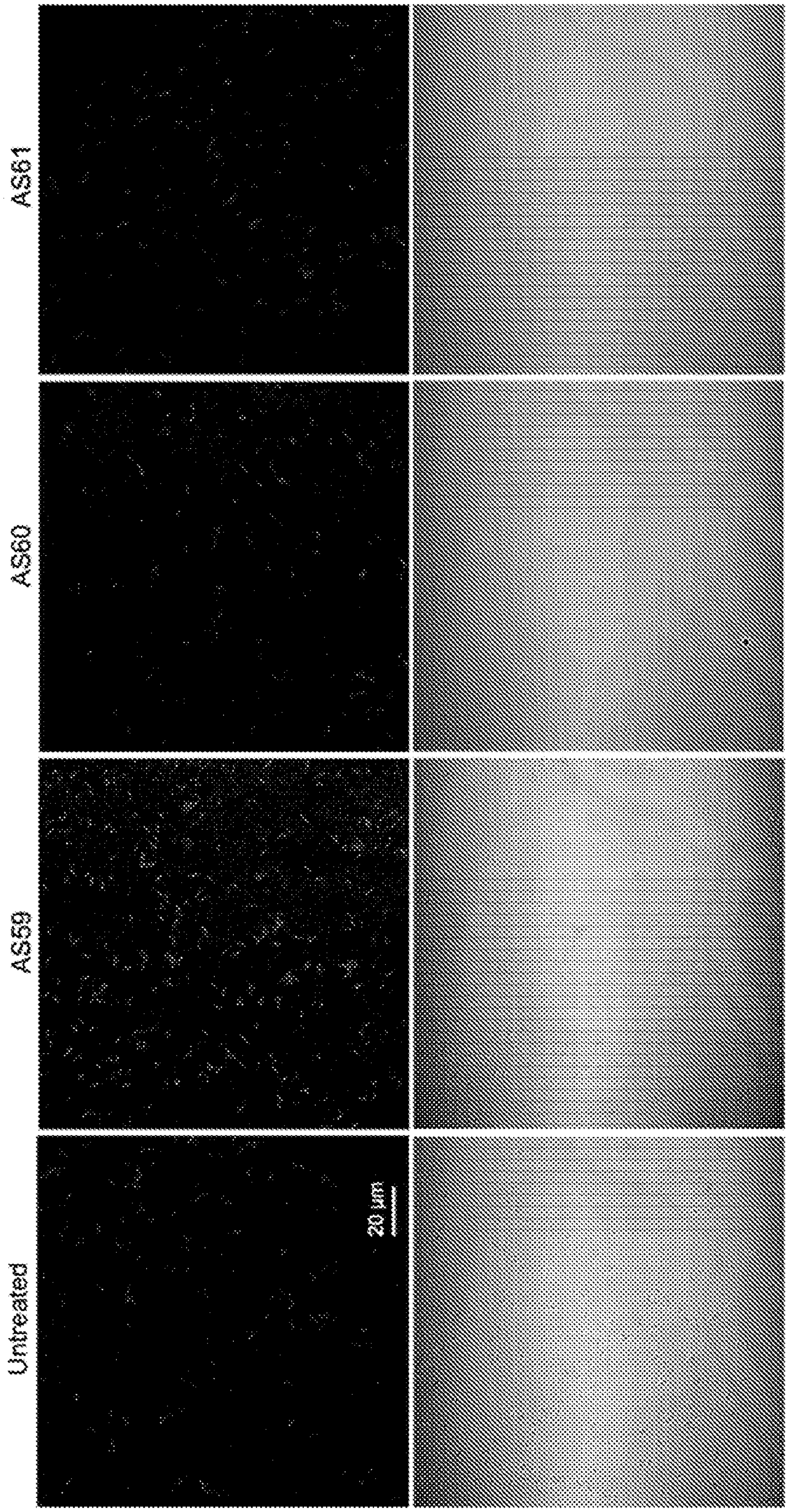
FIG. 10 shows internalization of Fn-targeting tsRNAs by *Fusobacterium nucleatum* (Fn25586), another Fuso species.

FIG. 10 shows internalization of Fn-targeting tsRNAs by *Fusobacterium nucleatum* (Fn25586), another Fuso species.

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A chemically modified tsRNA, wherein the chemically modified tsRNA is AS38

(SEQ ID NO: 3)
AS38 - [mC]*[mC]*[mG]GCUAGCUCAGUCGGUAGAGCAUG[mA]*[mG]*[mA] or (SEQ ID NO: 4)
AS39 - [mG]*[mG]*[mG]GGUAUAGCUCAGUGGGUAGAG[mC]*[mA]*[mU], wherein * refers to a phosphorothioate linkage (PS bond) and m refers to 2'-O-methyl (2'OMe).

2. The chemically modified tsRNA of claim 1, wherein the chemically modified tsRNA inhibits growth of *F. nucleatum.*

3. The chemically modified tsRNA of claim 1, wherein the chemically modified tsRNA increases growth inhibition of *Fusobacterium nucleatum* (Fn) compared to a naturally occurring tsRNA with the same sequence.

4. The chemically modified tsRNA of claim 1, wherein the chemically modified tsRNA does not inhibit growth of *Streptococcus mitis* or *Porphyromonas gingivalis.*

5. The chemically modified tsRNA of claim 1, wherein the chemically modified tsRNA is internalized by *Fusobacterium nucleatum* strain 23726 or 25586.

6. A pharmaceutical composition, comprising at least one chemically modified tsRNA of claim 1 and a pharmaceutically acceptable carrier.

7. The pharmaceutical composition of claim 6, comprising two chemically modified tsRNAs, wherein one is selected from AS38

(SEQ ID NO: 3)
AS38 - [mC]*[mC]*[mG]GCUAGCUCAGUCGGUAGAGCAUG[mA]*[mG]*[mA] and (SEQ ID NO: 1)
AS41 - CCGGCUAGCUCAGUCGGUAGAGCAUGAG[mA], and the other one is selected from AS39

(SEQ ID NO: 4)
AS39 - [mG]*[mG]*[mG]GGUAUAGCUCAGUGGGUAGAG[mC]*[mA]*[mU] and (SEQ ID NO: 2)
AS42 - GGGGGUAUAGCUCAGUGGGUAGAGCA[mU], wherein * refers to a phosphorothioate linkage (PS bond) and m refers to 2'-O-methyl (2'OMe).

8. The pharmaceutical composition of claim 7, wherein the two chemically modified tsRNAs are AS38 and AS39.

9. A chemically modified tsRNA, wherein the chemically modified tsRNA is AS38

(SEQ ID NO: 3)
AS38 - [mC]*[mC]*[mG]GCUAGCUCAGUCGGUAGAGCAUG[mA]*[mG]*[mA], wherein * refers to a phosphorothioate linkage (PS bond) and m refers to 2'-O-methyl (2'OMe).

10. A pharmaceutical composition, comprising the chemically modified tsRNA of claim 9 and a pharmaceutically acceptable carrier.

11. A chemically modified tsRNA, wherein the chemically modified tsRNA is AS39

(SEQ ID NO: 4)
AS39 - [mG]*[mG]*[mG]GGUAUAGCUCAGUGGGUAGAG[mC]*[mA]*[mU], wherein * refers to a phosphorothioate linkage (PS bond) and m refers to 2'-O-methyl (2'OMe).

12. A pharmaceutical composition, comprising the chemically modified tsRNA of claim 11 and a pharmaceutically acceptable carrier.

* * * * *